US011534072B2

(12) United States Patent
Higashimura et al.

(10) Patent No.: US 11,534,072 B2
(45) Date of Patent: Dec. 27, 2022

(54) SPHYGMOMANOMETER, BLOOD PRESSURE MEASUREMENT METHOD, AND DEVICE

(71) Applicants: OMRON CORPORATION, Kyoto (JP); OMRON HEALTHCARE CO., LTD., Muko (JP)

(72) Inventors: Yu Higashimura, Kyoto (JP); Takanori Nishioka, Kyoto (JP); Akira Tampo, Kyoto (JP); Yoshihiko Sano, Kyoto (JP); Takeshi Kubo, Kyoto (JP); Shohei Iwata, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 323 days.

(21) Appl. No.: 16/470,458

(22) Filed: Jun. 17, 2019

(65) Prior Publication Data
US 2019/0374115 A1 Dec. 12, 2019

Related U.S. Application Data

(63) Continuation of application No. PCT/JP2017/042083, filed on Nov. 22, 2017.

(30) Foreign Application Priority Data

Dec. 28, 2016 (JP) .............................. JP2016-256019

(51) Int. Cl.
*A61B 5/022* (2006.01)
*A61B 5/0225* (2006.01)
(Continued)

(52) U.S. Cl.
CPC ........ *A61B 5/02233* (2013.01); *A61B 5/0225* (2013.01); *A61B 5/681* (2013.01); *A61B 5/0235* (2013.01)

(58) Field of Classification Search
CPC ... A61B 5/02233; A61B 5/0225; A61B 5/681; A61B 5/0235; A61B 5/02141; A61B 5/02255
See application file for complete search history.

(56) References Cited

U.S. PATENT DOCUMENTS

| 6,336,901 B1 | 1/2002 | Itonaga et al. | |
| 2009/0234381 A1* | 9/2009 | Karo | ...................... A61B 5/742 606/202 |
| 2011/0112412 A1* | 5/2011 | Sano | .................. A61B 5/02233 600/499 |

FOREIGN PATENT DOCUMENTS

| CN | 1748637 A | 3/2006 |
| CN | 101346100 A | 1/2009 |

(Continued)

OTHER PUBLICATIONS

English-language machine translation of JP-2004350786-A (Year: 2021).*

(Continued)

*Primary Examiner* — Andrey Shostak
(74) *Attorney, Agent, or Firm* — Oliff PLC

(57) ABSTRACT

A sphygmomanometer includes: a sensing cuff that includes a second sheet disposed to face the pressing member's inner circumferential surface and a first sheet facing the second sheet; a fluid storage control part providing a control of supplying and storing the pressure-transmitting fluid into sensing cuff in a worn state wherein the pressing member and sensing cuff are worn on the wrist; and a blood-pressure calculating part calculating a blood pressure based on a pressure of the pressure-transmitting fluid stored in the sensing cuff. The fluid storage control part supplies fluid in the worn state such that the first and second sheets are in contact with each other in a region corresponding to an ulna, a region corresponding to a radius, and a region correspond- (Continued)

ing to a tendon while first and second sheets are separated from each other in regions corresponding to two arteries that are radial and ulnar arteries.

10 Claims, 17 Drawing Sheets

(51) Int. Cl.
 *A61B 5/00* (2006.01)
 *A61B 5/0235* (2006.01)

(56) References Cited

FOREIGN PATENT DOCUMENTS

| | | | |
|---|---|---|---|
| CN | 102088900 | A | 6/2011 |
| JP | S64-072726 | * | 3/1989 |
| JP | S64-072726 | A | 3/1989 |
| JP | H11-309119 | A | 11/1999 |
| JP | 2003-024286 | A | 1/2003 |
| JP | 2003-290156 | A | 10/2003 |
| JP | 2004-350786 | A | 12/2004 |
| JP | 2004350786 | A * | 12/2004 |
| JP | 2005-334124 | A | 12/2005 |
| JP | 2005334124 | A * | 12/2005 |
| JP | 2010-119447 | A | 6/2010 |
| WO | WO-9955400 | A1 * | 11/1999 ......... A61B 5/02233 |
| WO | 2011/122259 | A1 | 10/2011 |
| WO | WO-2011122259 | A1 * | 10/2011 ......... A61B 5/02233 |

OTHER PUBLICATIONS

English-language machine translation of WO-9955400-A1 (Year: 2021).*
English-language machine translation of JP-2005334124-A (Year: 2021).*
English-language machine translation of WO-2011122259-A1 (Year: 2021).*
English-language machine translation of JPS64-072726 (Year: 2021).*
Feb. 27, 2018 Search Report issued in International Application No. PCT/JP2017/042083.
Jun. 7, 2021 Office Action issued in Chinese Application No. 201780073101.3.
Nov. 8, 2021 Office Action issued in Chinese Patent Application No. 201780073101.3.

* cited by examiner

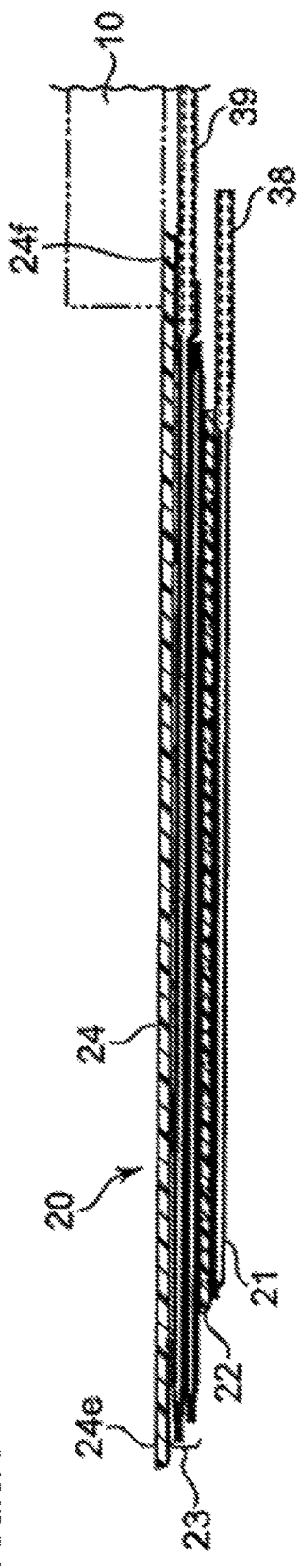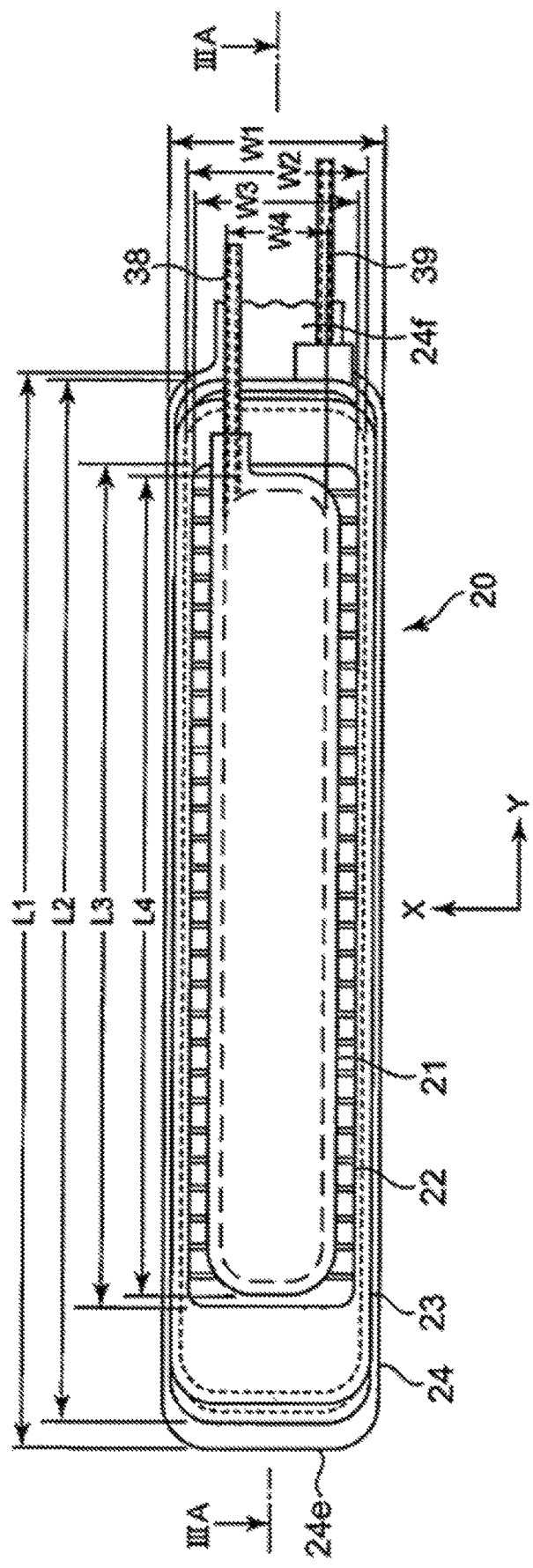
FIG.3A
FIG.3B

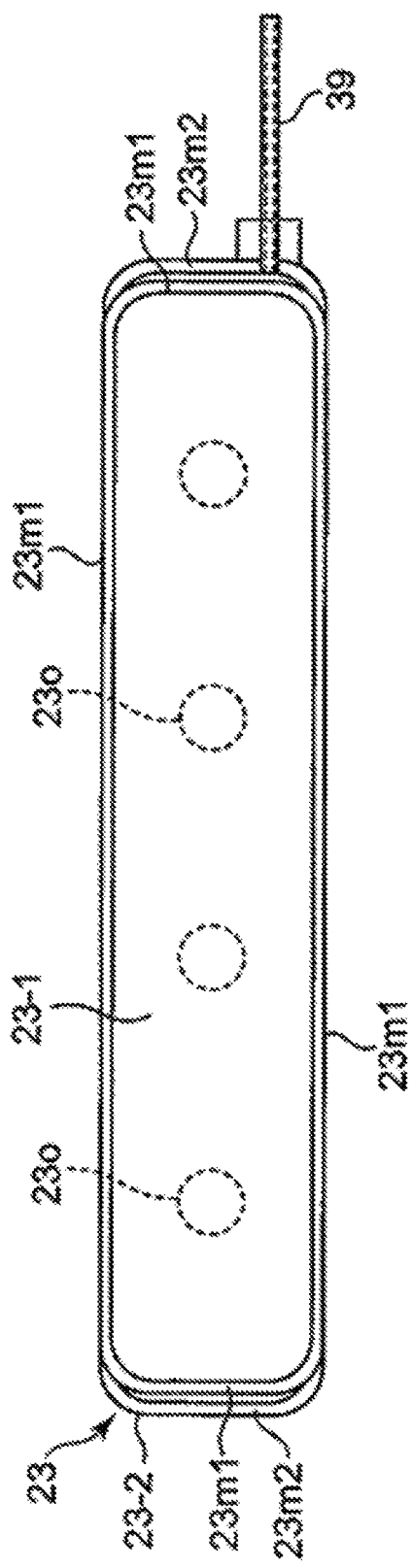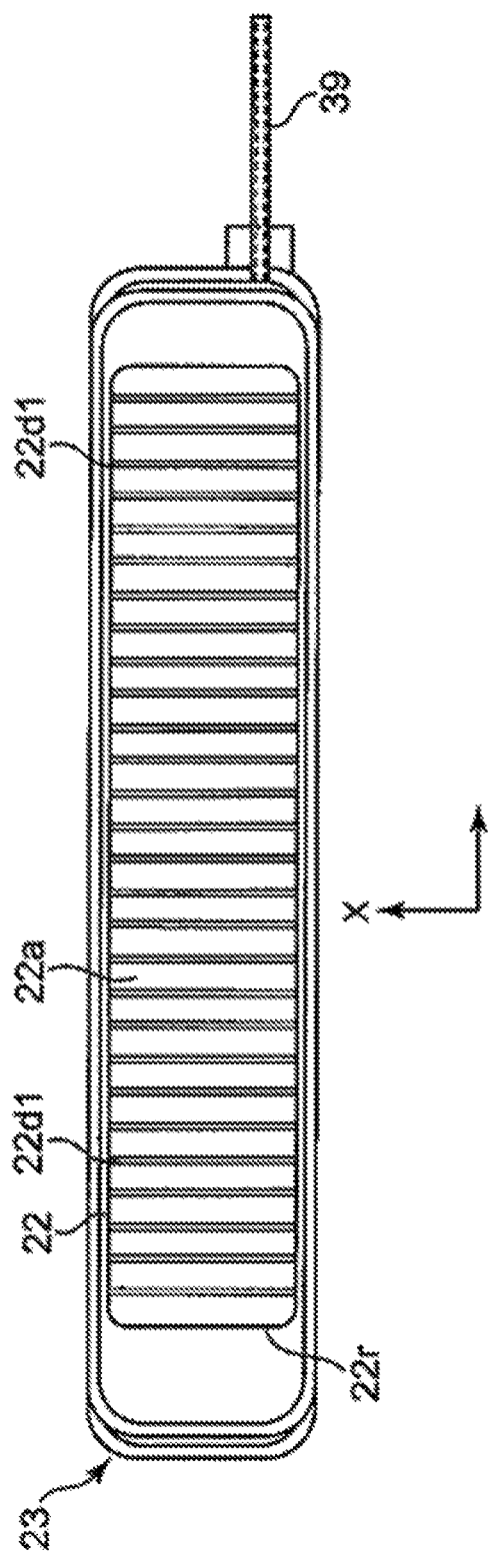

SPHYGMOMANOMETER, BLOOD PRESSURE MEASUREMENT METHOD, AND DEVICE

CROSS-REFERENCE TO RELATED APPLICATION

This is a continuation application of International Application No. PCT/JP2017/042083, with an International filing date of Nov. 22, 2017, which claims priority of Japanese Patent Application No. 2016-256019 filed on Dec. 28, 2016, the entire content of which is hereby incorporated by reference.

TECHNICAL FIELD

The present invention relates to a sphygmomanometer and, more particularly, to a sphygmomanometer comprising a belt worn to wrap a measurement site and a main body equipped with a pump. The present invention also relates to a blood-pressure measurement method for measuring a blood pressure at a measurement site. The present invention further relates to a device having a blood-pressure measurement function.

BACKGROUND ART

For example, as disclosed in Patent Document 1 (Japanese Laid-Open Patent Publication No. 11-309119), conventionally known sphygmomanometer of this type has a cuff wound around a wrist that is a measurement site, and a main body integrally attached to the cuff. This sphygmomanometer includes in a strap-shaped belt a bag-shaped blood-pressure measurement cuff compressing an artery, an intervening member disposed on the outside of the blood-pressure measurement cuff, and a bag-shaped pressing cuff disposed on the outside of the intervening member, and is configured to detect a pressure in the blood-pressure measurement cuff with a pressure sensor mounted on the main body. At the time of blood pressure measurement, a predetermined amount of air for pressurization is supplied from a pump mounted on the main body to the blood-pressure measurement cuff while the belt is worn to wrap the wrist, and subsequently, air is also supplied to the pressing cuff to compress the artery of the wrist (radial artery, ulnar artery). Based on an output of the pressure sensor, a blood pressure measurement value is calculated by an oscillometric method. In this sphygmomanometer, a predetermined amount of air is supplied to the blood-pressure measurement cuff, and a force for sufficiently compressing a living body site is achieved by the intervening member and the pressing cuff, so that a feeling of oppression or discomfort is eliminated while the cuff is worn.

SUMMARY OF THE INVENTION

To detect a pulse wave of a blood flow passing through an artery, the blood-pressure measurement cuff described above should detect pressures in the vicinity of the radial artery between the radius and the tendon of the flexor carpi radialis muscle and in the vicinity of the ulnar artery between the ulna and the tendon of the palmaris longus muscle in the wrist that is a measurement site (hereinafter, the tendon of the flexor carpi radialis and the tendon of the palmaris longus muscle are collectively referred to simply as "tendons").

However, in the sphygmomanometer, air is supplied to a blood-pressure measurement cuff to such an extent that the cuff is substantially flatly inflated over an entire area of a palmar side surface (surface on the palm side) of the wrist that is the measurement site at the time of blood pressure measurement. Therefore, the wrist is compressed not only in relatively soft portions such as the vicinities of the radial artery and the ulnar artery but also in relatively hard portions such as the radius, the ulna, and the tendons. In the wrist, a repulsive force from the relatively hard portions such as the radius, the ulna, and the tendons is higher than the repulsive forces from the relatively soft portions such as the vicinities of the radial artery and the ulnar artery. Therefore, the internal pressure of the blood pressure measurement cuff generally becomes higher than the pressure in the vicinities of the radial artery and the ulnar artery. This causes a problem that a measurement error of a blood pressure value becomes larger.

Therefore, an object of the present invention is to provide a sphygmomanometer, a blood-pressure measurement method, and a device capable of accurately measuring a blood pressure even when the blood pressure is measured on a measurement site that is the wrist by using a bag-shaped blood-pressure measurement cuff.

To achieve the object, a sphygmomanometer of the present disclosure is a sphygmomanometer comprising:

a pressing member disposed to wrap a wrist that is a measurement site in a circumferential direction and generating a pressing force toward the wrist;

a sensing cuff that includes a second sheet disposed to face an inner circumferential surface of the pressing member and a first sheet facing the second sheet, that is formed into a bag shape for storing a pressure-transmitting fluid with circumferential edge portions of the first and second sheets brought into close contact with each other, that extends in the circumferential direction to cross an artery-passing portion of the wrist, and that allows entire areas surrounded by the circumferential edge portions of the first and second sheets to separate from each other;

a pressurization control part providing a control of compressing the wrist by the pressing member via the sensing cuff;

a fluid storage control part providing a control of supplying and storing the pressure-transmitting fluid into the sensing cuff in a worn state in which the pressing member and the sensing cuff are worn on the wrist; and a blood-pressure calculating part calculating a blood pressure based on a pressure of the pressure-transmitting fluid stored in the sensing cuff, wherein the fluid storage control part supplies the fluid in the worn state such that the first and second sheets are in contact with each other in a region corresponding to an ulna, a region corresponding to a radius, and a region corresponding to a tendon while the first and second sheets are separated from each other in regions corresponding to two arteries that are radial and ulnar arteries, and wherein the pressurization control part provides the control of compressing the wrist by the pressing member via the sensing cuff in this state.

The pressurizing and pressure-transmitting "fluid" is typically air or may be another gas or liquid. The "pressure-transmitting fluid" may be stored in the sensing cuff at a manufacturing stage of the sphygmomanometer or may be stored in the sensing cuff and discharged from the sensing cuff each time a blood pressure is measured.

The "inner circumferential surface" of the pressing member refers to the surface on the inner circumferential side in the worn state in which the measurement site is wrapped.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 3B is a view showing a planar layout when a cuff structure of FIG. 2 is in a developed state with an inner circumferential surface on the forefront. FIG. 3A is a view showing a cross section taken along a line IIIA-IIIA of FIG. 3B as viewed in a direction of arrows.

FIG. 5A is a view showing a planar layout of a pressing cuff included in the cuff structure. FIG. 5B is a view showing a planar layout of a back plate included in the cuff structure with the pressing cuff in the background.

DESCRIPTION OF EMBODIMENT

Embodiments of the present invention will now be described in detail with reference to the drawings.
(Configuration of Sphygmomanometer)

Figure 1:
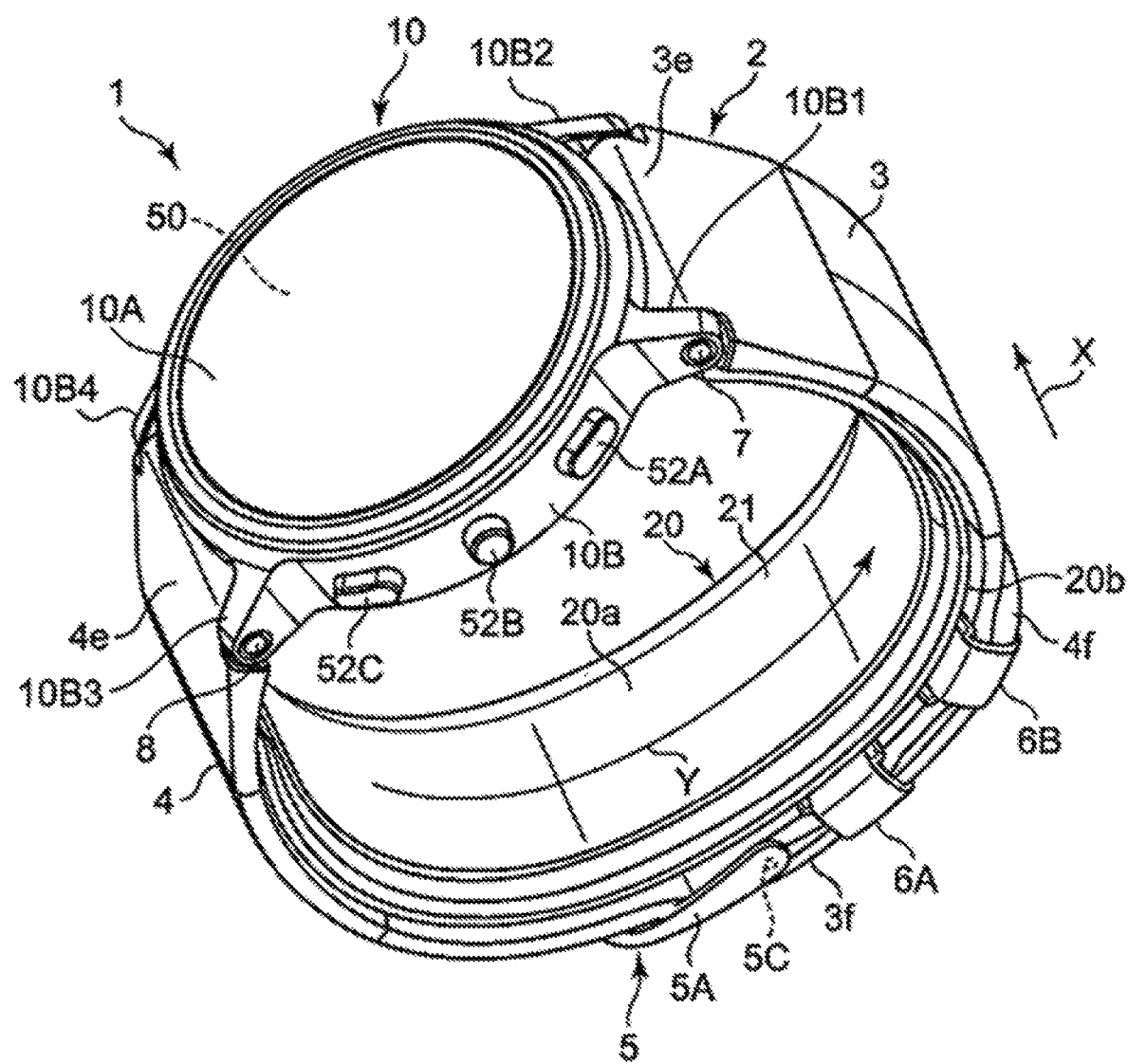
FIG. 1 is a view showing an appearance of a sphygmomanometer of an embodiment of the present invention with a belt fastened as viewed obliquely.
Figure 2:
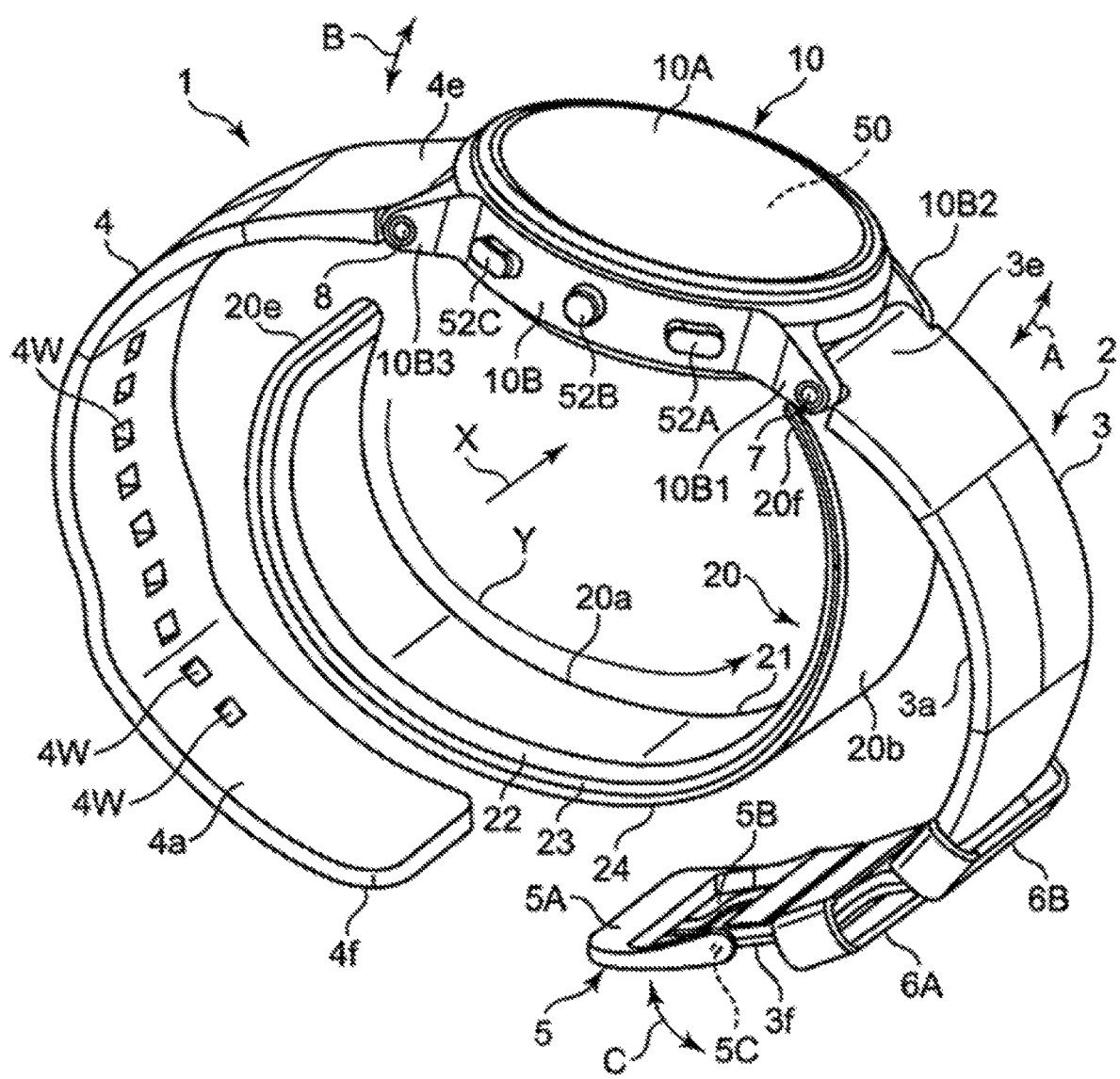
FIG. 2 is a view showing the appearance of the sphygmomanometer with the belt released as viewed obliquely.

FIG. 1 shows an appearance of a sphygmomanometer (generally denoted by reference numeral 1) of an embodiment of the present invention with a belt 2 fastened as viewed obliquely. FIG. 2 shows the appearance of the sphygmomanometer 1 with the belt 2 released as viewed obliquely.

Figure 13A:
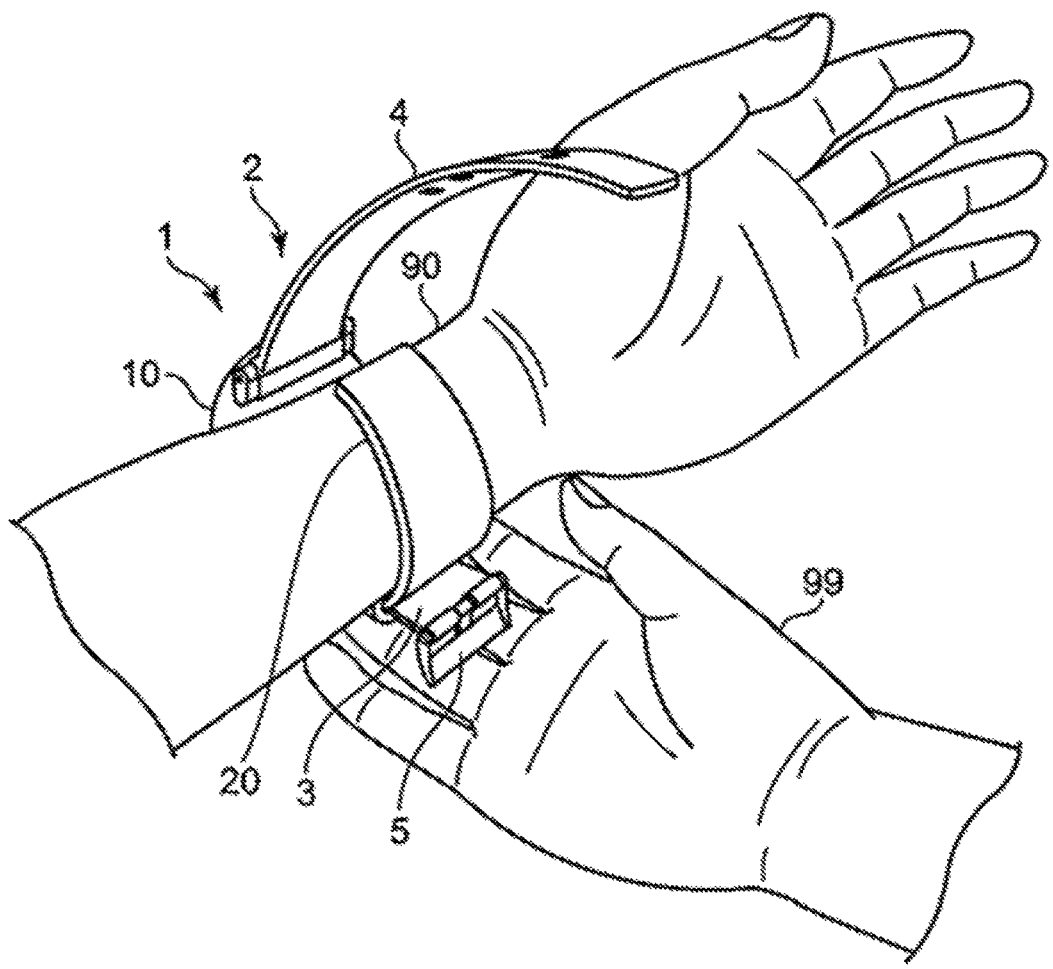
FIG. 13A is a perspective view showing a form when the user wears the cuff structure on the left wrist by using the right hand.
Figure 13B:
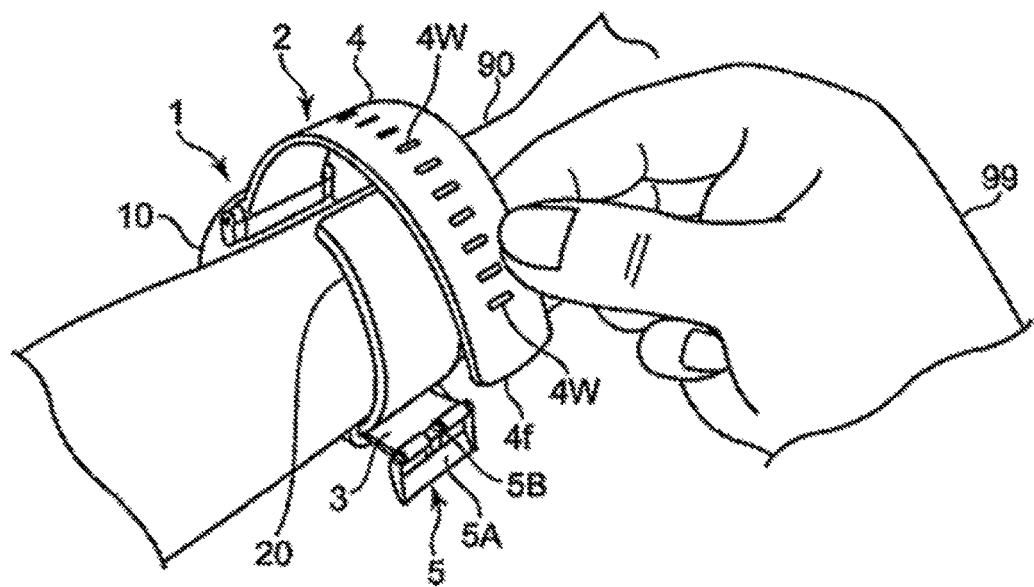
FIG. 13B is a perspective view showing a form when the user wraps the left wrist and the cuff structure with a belt together by using the right hand.
Figure 13C:
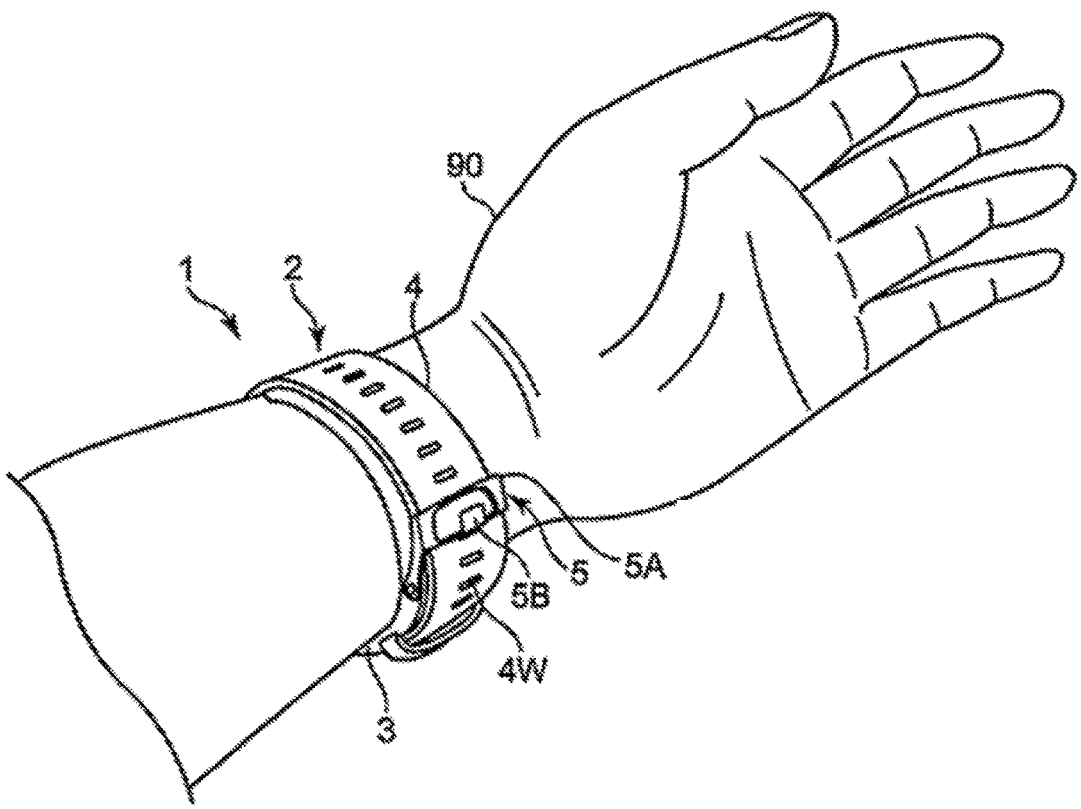
FIG. 13C is a perspective view showing a form when the sphygmomanometer is worn on the left wrist of the user.

As shown in these figures, the sphygmomanometer 1 roughly includes a main body 10, the belt 2 extended from the main body 10 and to be worn to wrap a measurement site (in this example, as shown in FIG. 13C described later, a left wrist 90 is supposed to be the measurement site), and a strap-shaped cuff structure 20 having one end 20f attached to the main body 10. The dimension in a width direction X of the belt 2 is set to 29 mm in this example. The thickness of the belt 2 is set to 2 mm in this example.

In this example, the main body 10 has a substantially short cylindrical-shaped case 10B, a circular glass 10A attached to an upper portion (in FIGS. 1 and 2) of the case 10B, and a back lid 10C (see FIG. 6) attached to a lower portion of the case 10B. A side surface of the case 10B is integrally provided with pairs of projecting lugs 10B1 and 10B2, 10B3 and 10B4 respectively on the left and right sides (in FIGS. 1 and 2) for attaching the belt 2.

A display 50 constituting a display screen is disposed inside the glass 10A of the upper portion of the case 10B. The side surface on the near side (in FIGS. 1 and 2) of the main body 10 is provided with a measurement switch 52A for giving an instruction for starting or stopping a blood pressure measurement, a home switch 52B for returning the display screen of the display 50 to a predetermined home screen, and a record calling switch 52C for instructing the display 50 to display past measurement records of blood pressure, activity amount, etc. (these switches are collectively referred to as an operation part 52). Additionally, blood-pressure measurement elements including a pump 30 are mounted inside the main body 10 (described in detail later). In this example, the sphygmomanometer 1 has functions of an activity amount meter and a pulsometer. Therefore, the sphygmomanometer 1 is configured as a multifunctional device having a form of a watch-type wearable device. The main body 10 is small-sized and thinly formed so as not to interfere with daily activities of a user.

As can be seen clearly from FIG. 2, the belt 2 has a strap-shaped first belt part 3 extending from the main body 10 to one side in one direction (right side in FIG. 2) and a strap-shaped second belt part 4 extending from the main body 10 to the other side in opposite direction (left side in FIG. 2). A root portion 3e of the first belt part 3 on the side closer to the main body 10 is attached pivotally as indicated by a double arrow A to the lugs 10B1, 10B2 of the main body 10 via a coupling rod 7 (known spring rod) extending in the width direction X of the belt. Similarly, a root portion 4e of the second belt part 4 on the side closer to the main body 10 is attached pivotally as indicated by a double arrow B to the lugs 10B3, 10B4 of the main body 10 via a coupling rod 8 (known spring rod) extending in the width direction X of the belt.

A buckle 5 is attached to a tip portion 3f of the first belt part 3 on the side far from the main body 10. The buckle 5 is of a known type and includes a substantially U-shaped frame-shaped body 5A, a prong 5B, and a coupling rod 5C extending in the width direction X of the belt. The frame-shaped body 5A and the prong 5B are both attached pivotally as indicated by a double arrow C to the tip portion 3f of the first belt part 3 on the side far from the main body 10 via the coupling rod 5C. A ring-shaped belt holding portions 6A, 6B are integrally disposed between the tip portion 3f and the root portion 3e of the first belt part 3 at positions predefined in a longitudinal direction of the first belt part 3 (corresponding to a circumferential direction Y of the left wrist 90). An inner circumferential surface 3a of the first belt part 3 does not protrude toward the inner circumferential side at the positions of the belt holding portions 6A, 6B and is basically formed flat (locally, although curved as a whole). Therefore, the belt 2 is designed to uniformly wrap and bind the outer circumferential side of the cuff structure 20.

Multiple small holes 4w, 4w . . . each penetrating in the thickness direction of the second belt part 4 are formed in the second belt part 4 between the root portion 4e and a tip portion 4f on the side far from the main body 10. When the first belt part 3 and the second belt part 4 are fastened, a portion leading to the tip portion 4f of the second belt part 4 is passed through the frame-shaped body 5A of the buckle 5, and the prong 5B of the buckle 5 is inserted through any one of the multiple small holes 4w, 4w . . . . As a result, the first belt part 3 and the second belt part 4 are fastened as shown in FIG. 1.

In this example, the first belt part 3 and the second belt part 4 constituting the belt 2 are made of a plastic material flexible in the thickness direction and substantially inelastic in the longitudinal direction (corresponding to the circumferential direction Y of the left wrist 90). Therefore, the belt 2 can easily wrap and bind the outer circumferential side of the cuff structure 20 at the time of wearing and can assist compression of the left wrist 90 at the time of blood pressure measurement described later. The first belt part 3 and the second belt part 4 may be made of a leather material. The frame-shaped body 5A and the prong 5B constituting the buckle 5 are made of a metal material in this example or may be made of a plastic material.

As shown in FIG. 2, the cuff structure 20 includes a curler 24 disposed on an outermost circumference, a pressing cuff 23 disposed along an inner circumferential surface of the curler 24, a back plate 22 serving as a reinforcing plate disposed along an inner circumferential surface of the pressing cuff 23, and a sensing cuff 21 disposed along an inner circumferential surface of the back plate 22. In this embodiment, the belt 2 described above, the curler 24, the pressing cuff 23, and the back plate function as pressing members capable of generating a pressing force toward the wrist, and the wrist is compressed via the sensing cuff 21 by these pressing members.

Figure 4A:
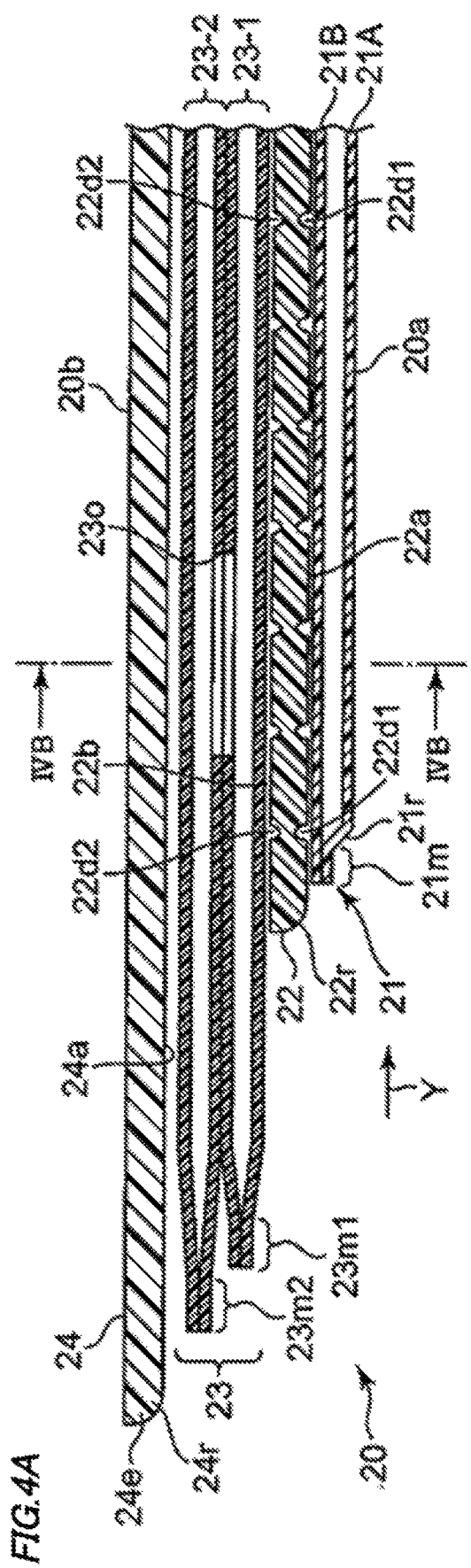
FIG. 4A is an enlarged view showing the vicinity of a tip portion of the cuff structure of FIG. 3B.
Figure 4B:
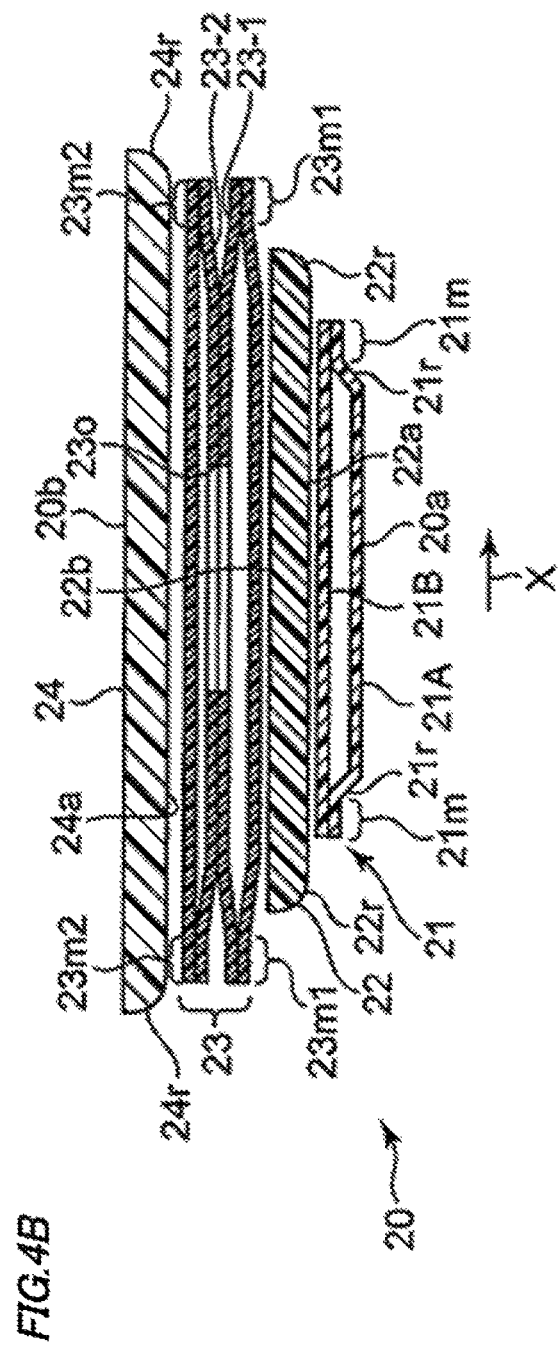
FIG. 4B is a view showing a cross section taken along a line IVB-IVB of FIG. 4A as viewed in a direction of arrows.

FIG. 3B shows a planar layout when the cuff structure 20 of FIG. 2 is in a developed state with an inner circumferential surface 20a on the forefront. FIG. 3A shows a cross section taken along a line IIIA-IIIA of FIG. 3B as viewed in a direction of arrows. FIG. 4A shows an enlarged view of the vicinity of a tip portion of the cuff structure 20 of FIG. 3B. FIG. 4B shows a cross section taken along a line IVB-IVB of FIG. 4A as viewed in a direction of arrows. FIG. 5A shows a planar layout of the pressing cuff 23. FIG. 5B shows a planar layout of the back plate 22 with the pressing cuff 23 in the background.

As shown in FIGS. 3A and 3B, the curler 24, the pressing cuff 23, the back plate 22, and the sensing cuff 21 each have a strap shape elongated in one direction (Y direction). In this example, the curler 24 has a dimension in the width direction X set to W1=28 mm, the pressing cuff 23 has a dimension in the width direction X (excluding welded edge portions on both sides) set to W2=25 mm, the back plate 22 has a dimension in the width direction X set to W3=23 mm, and sensing cuff 21 has a dimension in the width direction X (excluding welded edge portions on both sides) set to W4=15 mm. The curler 24 has a dimension in the longitudinal direction Y (excluding a root portion 24f attached to the main body 10) set to L1=148 mm, the pressing cuff 23 has a dimension in the longitudinal direction Y set to L2=140 mm, the back plate 22 has a dimension in the longitudinal direction Y set to L3=114 mm, and the sensing cuff 21 has a dimension in the longitudinal direction Y set to L4=110 mm.

As can be seen from FIGS. 4A and 4B, the sensing cuff 21 includes a first sheet 21A on the side in contact with the left wrist 90 and a second sheet 21B facing the first sheet 21A. The second sheet 21B is disposed to face the inner circumferential surface of the back plate 22 constituting the pressing member. Circumferential edge portions 21m of the first and second sheets 21A, 21B are brought into close contact with each other by welding and formed into a bag shape. In this example, as shown in FIG. 4B, sags 21r, 21r extending along the longitudinal direction Y of the sensing cuff 21 are disposed in a natural state at positions leading to the edge portions 21m, 21m on both sides in the width direction X of the sensing cuff 21. Additionally, as shown in FIG. 4A, sags 21r extending along the width direction X of the sensing cuff 21 are disposed in the natural state in the first sheet 21A at positions leading to the edge portions 21m on both sides in the longitudinal direction Y of the sensing cuff 21 (only a leading end side is shown in FIG. 4A). The sags 21r as described above may be formed by a known method, for example, when the circumferential edge portions 21m of the first and second sheets 21A, 21B are welded and brought into close contact with each other. As can be seen from FIGS. 3A and 3B, to an end portion on the root side (+Y side) in the longitudinal direction Y of the sensing cuff 21, a flexible tube 38 is attached for supplying a pressure-transmitting fluid (air in this example) to the sensing cuff 21 or discharging the pressure-transmitting fluid from the sensing cuff 21. The material of the first and second sheets 21A, 21B is an elastic polyurethane sheet (thickness t=0.15 mm) in this example. The inner circumferential surface 20a of the cuff structure 20 is made up of the first sheet 21A of the sensing cuff 21.

As used herein, "being in contact" includes not only direct contact but also indirect contact via another member (e.g., a cover member).

As can be seen from FIGS. 4A and 4B, the pressing cuff 23 includes two fluid bags 23-1, 23-2 stacked in the thickness direction. Each of the fluid bags 23-1, 23-2 is formed by welding circumferential edge portions 23m1, 23m2 of two elastic polyurethane sheets (thickness t=0.15 mm) faced each other. As shown in FIG. 5A, the dimension in the longitudinal direction Y of the fluid bag 23-1 on the inner circumferential side is set slightly smaller than the dimension (L2) in the longitudinal direction Y of the fluid bag 23-2 on the outer circumferential side. To an end portion on the root side (+Y side) in the longitudinal direction Y of the fluid bag 23-2 on the outer circumferential side, a flexible tube 39 is attached for supplying a pressure-transmitting fluid (air in this example) to the pressing cuff 23 or discharging the pressure-transmitting fluid from the pressing cuff 23. Multiple (four in this example) through-holes 23o, 23o . . . are formed between the fluid bag 23-1 on the inner circumferential side and the fluid bag 23-2 on the outer circumferential side adjacent thereto. Therefore, a pressurizing fluid (air in this example) can flow between the two fluid bags 23-1, 23-2 through the through-holes 23o, 23o. As a result, when the pressing cuff 23 in a worn state receives the supply of the pressurizing fluid from the main body 10 side through the flexible tube 39, the two stacked fluid bags 23-1, 23-2 expand to compress the left wrist 90 as a whole.

Figure 12:
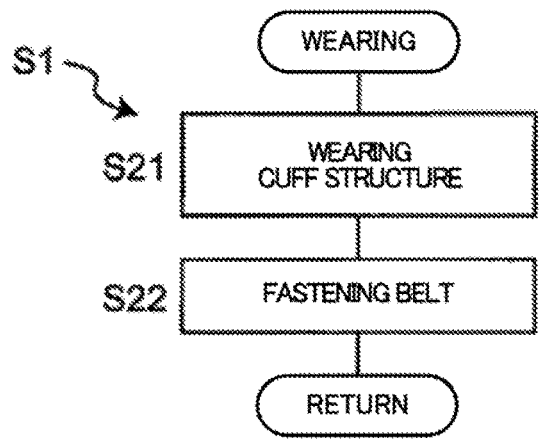
FIG. 12 is a diagram showing a flow of a process when the user wears the sphygmomanometer on the left wrist.

The back plate 22 is made up of a plate-shaped resin (polypropylene in this example) having a thickness of about 1 mm in this example. As can be seen from FIGS. 3A and 3B, the back plate 22 extends in a strap shape beyond the length of the sensing cuff 21 in the longitudinal direction Y (corresponding to the circumferential direction of the left wrist 90). Therefore, the back plate 22 can function as a reinforcing plate to transmit the pressing force from the pressing cuff 23 to an entire region in the longitudinal direction Y of the sensing cuff 21 (corresponding to the circumferential direction of the left wrist 90). As can be seen from FIGS. 4A and 5B, multiple grooves 22d1, 22d2 having V-shaped or U-shaped cross sections and extending in the width direction X are disposed on an inner circumferential surface 22a and an outer circumferential surface 22b of the back plate 22 and parallelly separated from each other in the longitudinal direction Y. In this example, the grooves 22d1, 22d2 are disposed at the same positions corresponding to each other between the inner circumferential surface 22a and the outer circumferential surface 22b of the back plate 22. As a result, the back plate 22 is made thinner and easier to bend at the positions of the grooves 22d1, 22d2 as compared to the other positions. Therefore, when the user brings the left wrist 90 and the cuff structure 20 into a state of being wrapped with the belt 2 together at the time of wearing (step S22 in FIG. 12 described later), the back plate 22 does not prevent the cuff structure 20 from curving along the circumferential direction Y of the left wrist 90.

Figure 7:
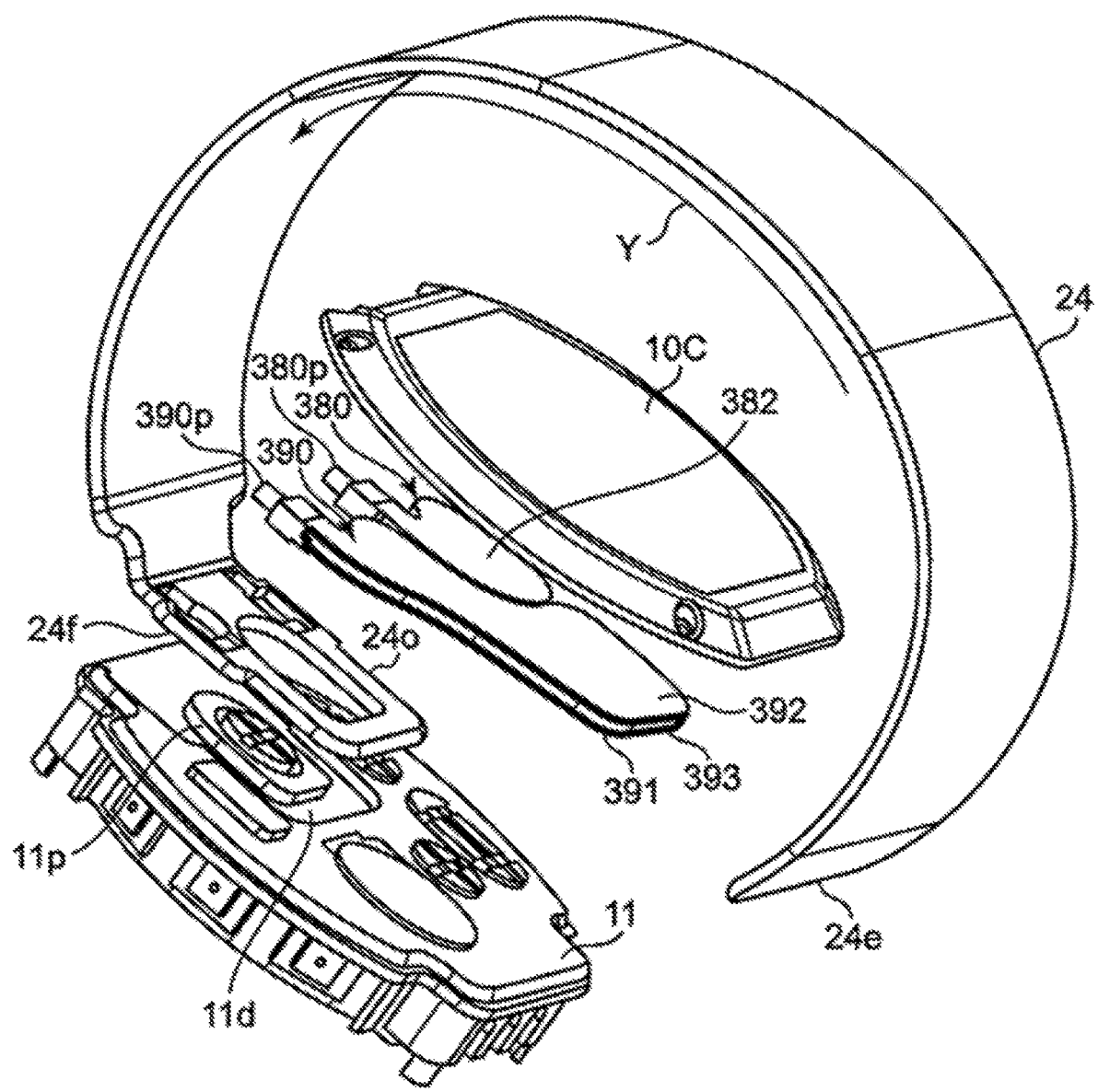
FIG. 7 is a view showing the back side of the main body in a disassembled state with a back lid removed, including a curler included in the cuff structure.

The curler 24 is made up of a plate of resin (polypropylene in this example) having certain degrees of flexibility and hardness and a thickness of about 1 mm in this example. As can be seen from FIGS. 3A and 3B, the curler 24 in the developed state extends in a strap shape beyond the length of the pressing cuff 23 in the longitudinal direction Y (corresponding to the circumferential direction of the left wrist 90). As shown in FIG. 7, the curler 24 has a curved shape along the circumferential direction Y surrounding the left wrist 90 in the natural state. As a result, the shape of the cuff structure 20 in the natural state is kept curved along the circumferential direction Y of the left wrist 90 as shown in FIG. 2.

A circumferential edge portion of the inner circumferential surface 22a of the back plate 22 and a circumferential edge portion of an inner circumferential surface 24a of the curler 24 are provided with respective curves 22r, 24r curved in a direction away from the measurement site (the left wrist 90 in this example). This prevents the user from having a feeling of discomfort due to wearing of the cuff structure 20.

Figure 6:
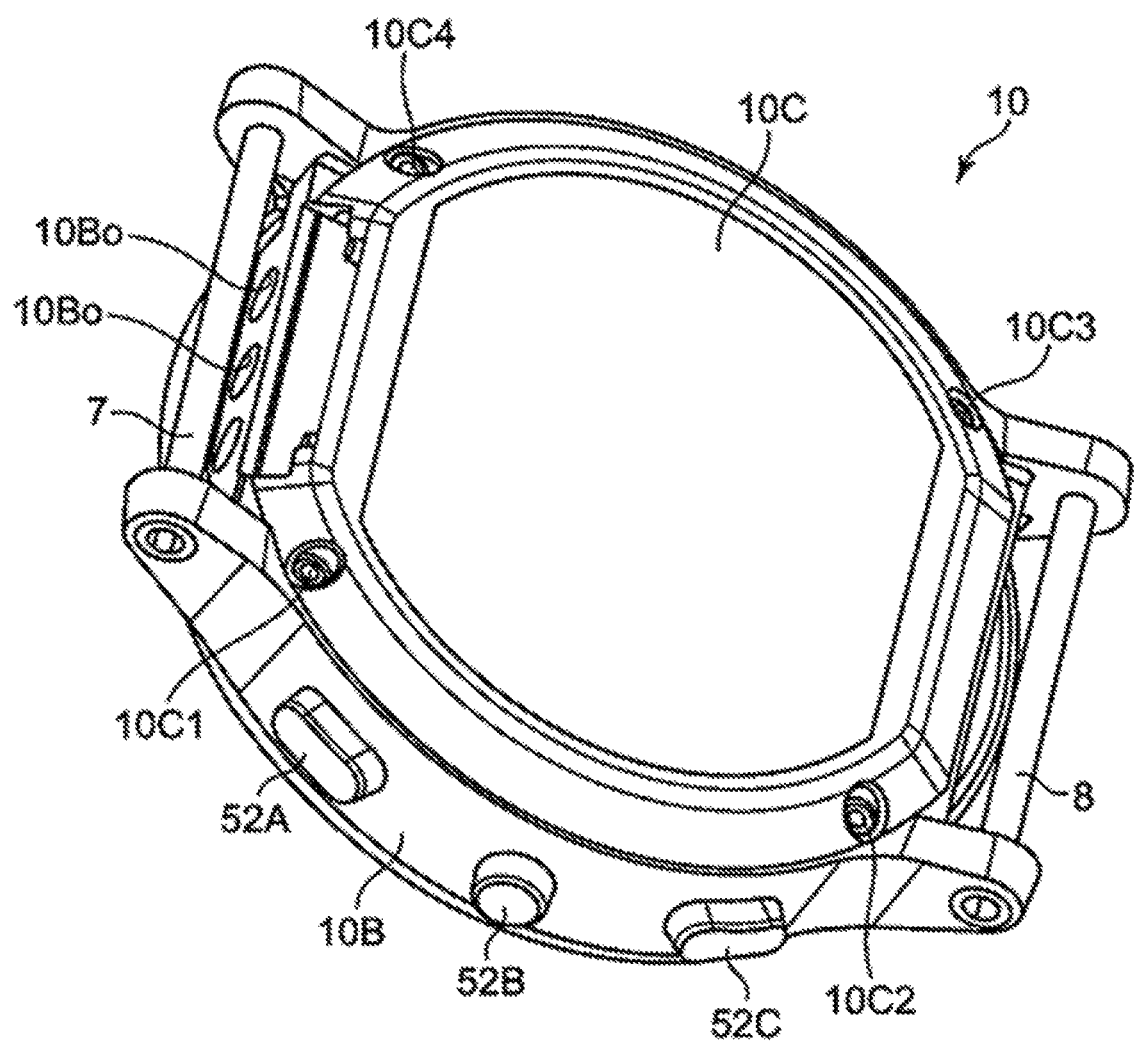
FIG. 6 is a view showing a back side of a main body of the sphygmomanometer as viewed obliquely.

As shown in FIG. 6, a back lid 10C is disposed on the back side of the main body 10. The back lid 100 has four through-holes 10C1, 10C2, 10C3, 10C4 and is fixed to the back side of the case 10B by screws not shown through the through-holes 10C1, 10C2, 10C3, 10C4. Intake/exhaust holes 10Bo, 10Bo with filters are disposed in a portion hidden by the root portion 3e of the first belt part 3 in the side surface of the case 10B (the same applies to a portion hidden by the root portion 4e of the second belt 4). This allows air to flow between the inside and the outside of the case 10B while a water-resistant function is implemented.

FIG. 7 shows the back side of the main body 10 in a disassembled state with the back lid 10C removed, including a curler 24 described above. In the case 10B of the main body 10, an inner case member 11 for mounting the blood-pressure measurement elements is stored. The back side of the inner case member 11 has an annular groove 11d formed to surround a periphery of a protrusion 11p. A ring 24o having a shape corresponding to the annular groove 11d is formed at the root portion 24f of the curler 24. When the main body 10 is assembled, the ring 24o of the root portion 24f of the curler 24 is fitted into the annular groove 11d of the inner case member 11 (at the same time, the ring 24o is fitted to the protrusion lip of the inner case member 11). The root portion 24f of the curler 24 is then sandwiched between the back side of inner case member 11 and the back lid 10C of the main body 10, while overlapping with two flow-path forming members (a first flow-path forming member 390 and a second flow-path forming member 380) described later.

As a result, as shown in FIG. 2, the one end 20f of the cuff structure 20 (the root portion 24f of the curler 24) is attached to the main body 10. The other end 20e of the cuff structure 20 (a tip portion 24e of the curler 24) is a free end. Consequently, the cuff structure 20 faces the inner circumferential surfaces 3a, 4a of the belt 2 and can be separated from the inner circumferential surfaces 3a, 4a.

When the cuff structure 20 is attached to the main body 10 in this way, the one end 20f of the cuff structure 20 is reliably held by the main body 10. At the time of maintenance service, the cuff structure 20 can be replaced for the main body 10 independently of the belt 2 by opening the back lid 10C of the main body 10. The dimension in the longitudinal direction Y (corresponding to the circumferential direction of the left wrist 90) of the cuff structure 20 may be set to an optimum dimension independently of the belt 2.

In the sphygmomanometer 1, the main body 10 and the belt 2 are formed separately from each other, and the belt 2 is attached to the main body 10, and therefore, the belt 2 can be replaced for the main body 10 independently of the cuff structure 20 at the time of maintenance service.

Figure 9:
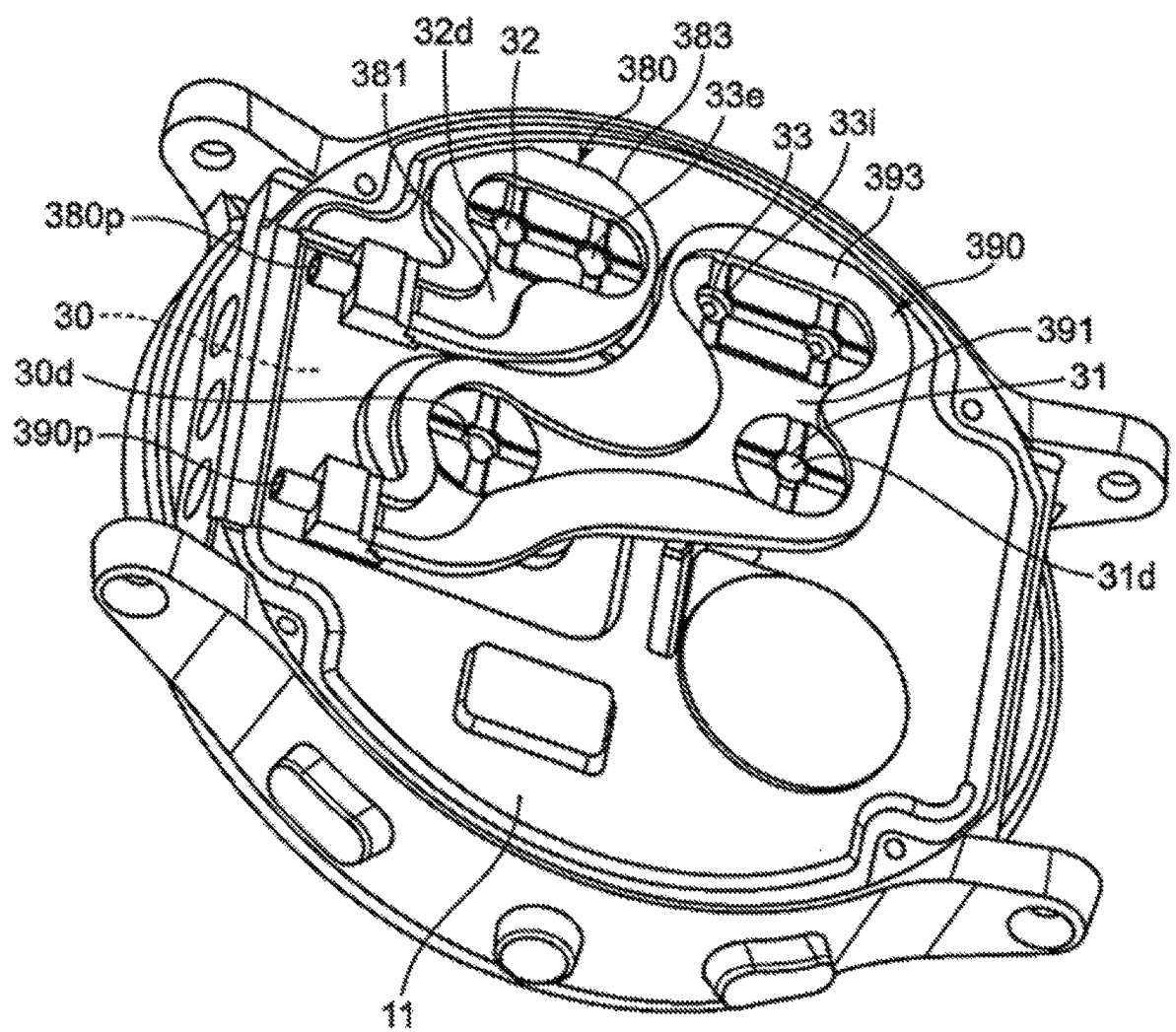
FIG. 9 is a view showing the inside of the main body as viewed obliquely from below.

The first flow-path forming member 390 shown in FIG. 7 is made up of two sheet plates 391, 392 facing each other and extending in a thin plate shape, and a spacer part 393 keeping a predefined interval (0.7 mm in this example) between these sheet plates 391, 392. Similarly, the second flow-path forming member 380 is made up of two sheet plates 381, 382 facing each other and extending in a thin plate shape, and a spacer part 383 keeping a predefined interval between these sheet plates 381, 382. The sheet plate 381 and the spacer part 383 are shown in FIG. 9 (in FIG. 9, the sheet plates 392, 382 on the side far from the inner case member 11 are omitted for facilitating understanding; FIG. 9 will be described later). Lateral pins 390p and 380p are integrally attached to an end portion of the first flow-path forming member 390 and an end portion of the second flow-path forming member 380, respectively, in a manner allowing a fluid to flow. When the cuff structure 20 including the curler 24 is attached to the main body 10, the flexible tube 39 from the pressing cuff 23 is connected via the lateral pin 390p to the first flow-path forming member 390. The flexible tube 38 from the sensing cuff 21 is connected via the lateral pin 380p to the second flow-path forming member 380.

The first flow-path forming member 390 and the second flow-path forming member 380 are formed by integral molding of an elastomer in this example. The thickness dimensions of the first flow-path forming member 390 and the second flow-path forming member 380 are set to 1.2 mm in this example.

Figure 10:
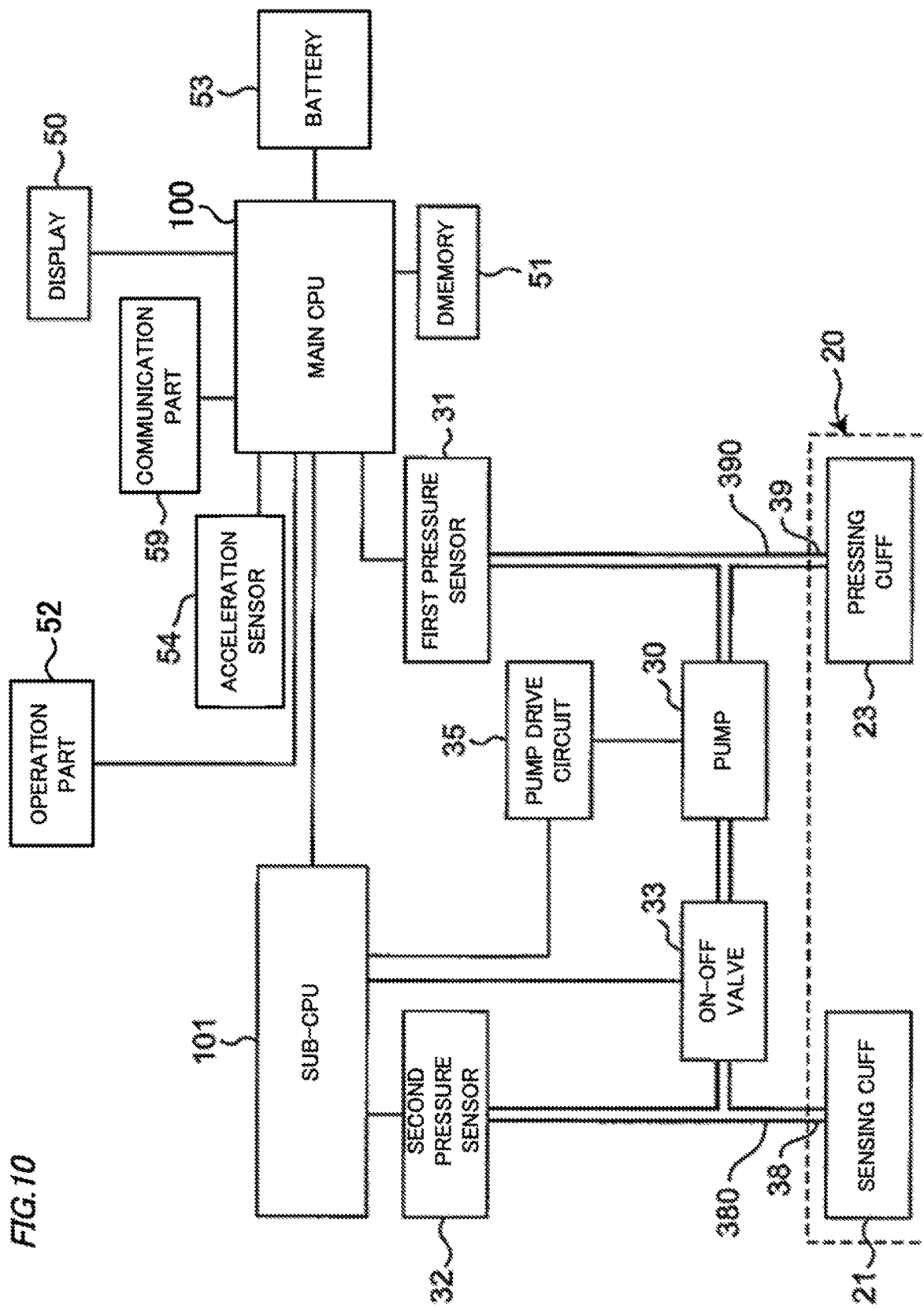
FIG. 10 is a diagram showing a block configuration of a control system of the sphygmomanometer.

FIG. 10 shows a block configuration of a control system of the sphygmomanometer 1. The main body 10 of the sphygmomanometer 1 is equipped with, in addition to the display 50 and the operation part 52 described above, as the blood-pressure measurement elements for performing a blood pressure measurement, a main CPU (central processing unit) 100 serving as a control part, a sub-CPU 101, a memory 51 serving as a storage part, an acceleration sensor 54, a communication part 59, a battery 53, a first pressure sensor 31 for detecting the pressure of the pressing cuff 23, a second pressure sensor 32 for detecting the pressure of the sensing cuff 21, the pump 30, an on-off valve 33, and a pump drive circuit 35 driving the pump 30. The main CPU 100 mainly controls the operation of the entire sphygmomanometer 1, and the sub-CPU 101 mainly controls the operation of an air system. Hereinafter, for simplicity, the main CPU 100 and the sub-CPU 101 will collectively be referred to simply as the CPU 100.

The display 50 is made up of an LCD (liquid crystal display) in this example and displays information on blood pressure measurement such as a blood pressure measurement result and other information in accordance with a control signal from the CPU 100. The display 50 is not limited to the organic EL display and may be another type of the display 50, for example, an organic EL (electro luminescence) display. The display 50 may include an LED (light emitting diode).

As described above, the operation part 52 includes the measurement switch 52A for giving an instruction for starting or stopping a blood pressure measurement, the home switch 52b for returning the display screen of the display 50 to a predetermined home screen, and the record calling switch 52C for instructing the display 50 to display past measurement records of blood pressure, activity amount, etc. In this example, these switches 52A to 52C are made up of push switches and input operation signals to the CPU 100 in accordance with an instruction for starting or stopping a blood pressure measurement from the user. The operation part 52 is not limited to the push switches, and may be, for example, pressure-sensitive (resistive) or proximity (electrostatic-capacitive) touch-panel switches. Additionally, a microphone not shown may be included for input of an instruction for starting a blood pressure measurement through a user's voice.

The memory 51 non-transitory stores data of a program for controlling the sphygmomanometer 1, data used for controlling the sphygmomanometer 1, setting data for setting various functions of the sphygmomanometer 1, data of measurement results of blood pressure values, etc. The memory 51 is also used as a work memory etc. when a program is executed.

The CPU 100 executes various functions as the control part in accordance with a program for controlling the sphygmomanometer 1 stored in the memory 51. For example, when executing the blood-pressure measurement function, the CPU 100 provides a control of driving the pump 30 and the on-off valve 33 based on signals from the first pressure sensor 31 and the second pressure sensor 32 in accordance with the instruction for starting a blood pressure measurement from the measurement switch 52A of the operation part 52. The CPU 100 also provides a control of calculating a blood pressure value, a pulse, etc. based on a signal from the second pressure sensor 32.

The acceleration sensor 54 is made up of a three-axis acceleration sensor integrally built in the main body 10. The acceleration sensor 54 outputs to the CPU 100 an acceleration signal indicative of the accelerations of the main body 10 in three directions orthogonal to each other. In this example, the output of the acceleration sensor 54 is used for measuring an activity amount.

The communication part 59 is controlled by the CPU 100 to transmit predetermined information through a network to an external apparatus or to receive information from the external apparatus through the network and deliver the information to the CPU 100. The communication through the network may be either wireless or wired. In this embodiment, the network is the Internet; however, the present invention is not limited thereto, and the network may be another type of network such as an intra-hospital LAN (local area network) or may be a one-to-one communication using a USB cable etc. The communication part 59 may include a micro USB connector.

The battery 53 is made up of a rechargeable secondary battery in this example. The battery 53 supplies electric power to the elements mounted on the main body 10, i.e., the CPU 100, the memory 51, the acceleration sensor 54, the communication part 59, the first pressure sensor 31, the second pressure sensor 32, the pump 30, the on-off valve 33, and the pump drive circuit 35 in this example.

The pump 30 is made up of a piezoelectric pump in this example and is driven by the pump drive circuit 35 based on a control signal supplied from the CPU 100. The pump 30 is connected via the first flow-path forming member 390 and the flexible tube 39 constituting a first flow path to the pressing cuff 23 in a manner allowing a fluid to flow. The pump 30 can supply air as a pressurizing fluid to the pressing cuff 23 through the first flow-path forming member 390 and the flexible tube 39. The pump 30 is equipped with an exhaust valve (not shown) controlled to open and close in accordance with on/off of the pump 30. Specifically, when the pump 30 is turned on, the exhaust valve closes to assist enclosing air in the pressing cuff 23, and when the pump 30 is turned off, the exhaust valve opens to discharge the air in the pressing cuff 23 to the atmosphere through the flexible tube 39 and the first flow-path forming member 390. This exhaust valve has a function of a check valve so that the air to be discharged does not flow backward.

The pump 30 is connected via the second flow-path forming member 380 and the flexible tube 38 constituting a second flow path to the sensing cuff 21 in a manner allowing a fluid to flow. The on-off valve (normally open solenoid valve in this example) 33 is interposed in the second flow path (actually, between the first flow-path forming member 390 and the second flow-path forming member 380). The opening/closing (opening degree) of the on/off valve 33 is controlled based on a control signal supplied from the CPU 100. When the on-off valve 33 is in an opened state, air can be supplied and stored as pressure-transmitting fluid from the pump 30 through the second flow path to the sensing cuff 21.

The first pressure sensor 31 and the second pressure sensor 32 are each made up of a piezoresistive pressure sensor in this example. The first pressure sensor 31 detects the pressure in the pressing cuff 23 via the first flow-path forming member 390 and the flexible tube 39 constituting the first flow path. The second pressure sensor 32 detects the pressure in the sensing cuff 21 via the second flow-path forming member 380 and the flexible tube 38 constituting the second flow path.

Figure 8:
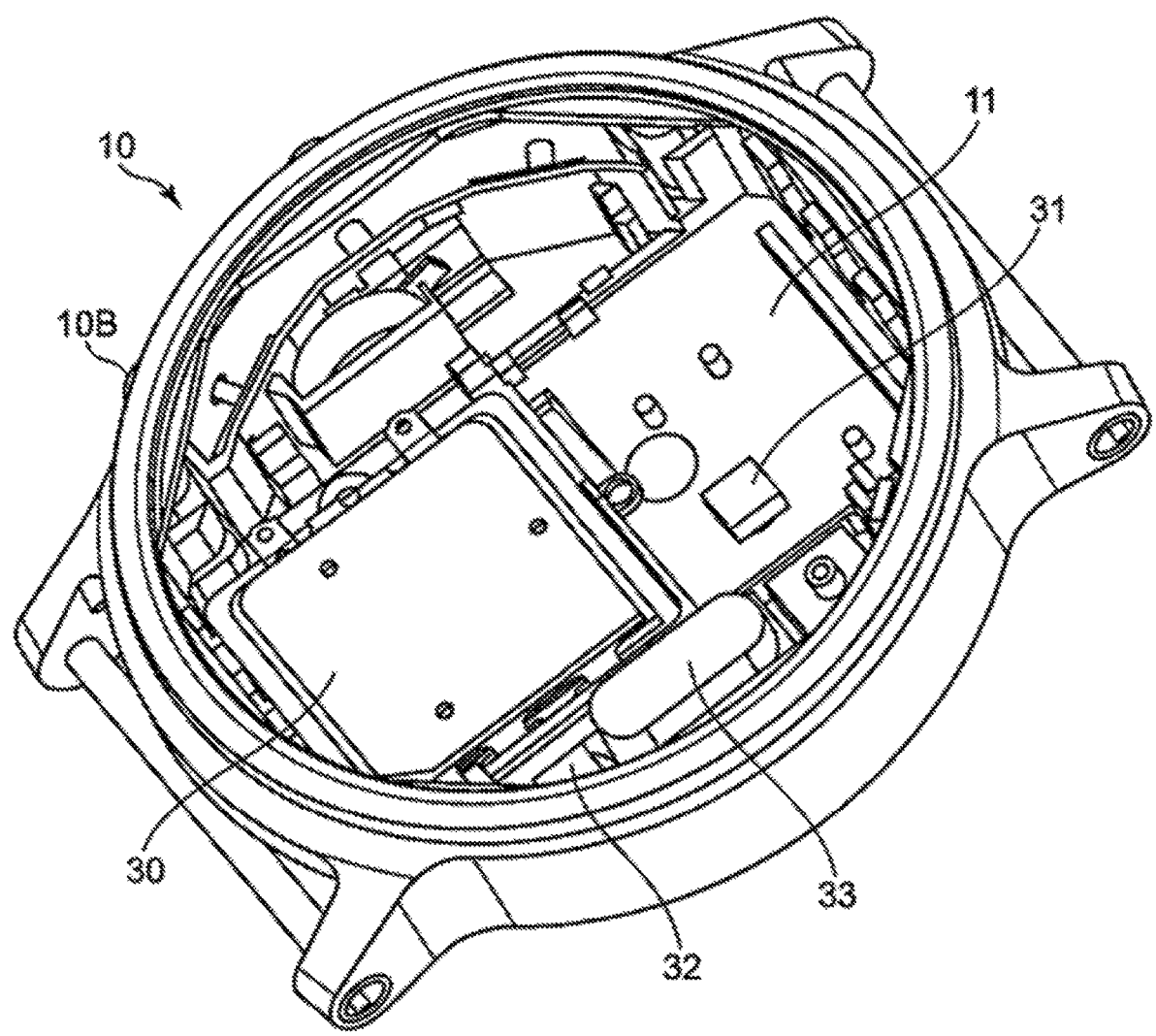
FIG. 8 is a view showing the inside of the main body as viewed obliquely from above.

As shown in FIG. 8 (when the inside of the main body 10 is viewed obliquely from above), the pump 30 and the first pressure sensor 31 are disposed substantially at the center of the inner case member 11 in the main body 10. The on-off valve 33 and the second pressure sensor 32 are disposed around the inner case member 11. As shown in FIG. 9 (when the inside of the main body 10 is viewed obliquely from below), the first flow-path forming member 390 is disposed on the back side of the inner case member 11 to extend over a discharge port 30d of the pump 30, an air introducing port 31d of the first pressure sensor 31, an inlet 33i of the on-off valve 33. The second flow-path forming member 380 is disposed on the back side of the inner case member 11 to extend over an outlet 33e of the on-off valve 33 and an air introducing port 32d of the second pressure sensor 32.

The sphygmomanometer 1 is small-sized and integrally formed by mounting the blood-pressure measurement elements as described above on the main body 10. Therefore, the usability for the user is good.

(Operation of Blood Pressure Measurement)

Figure 11:
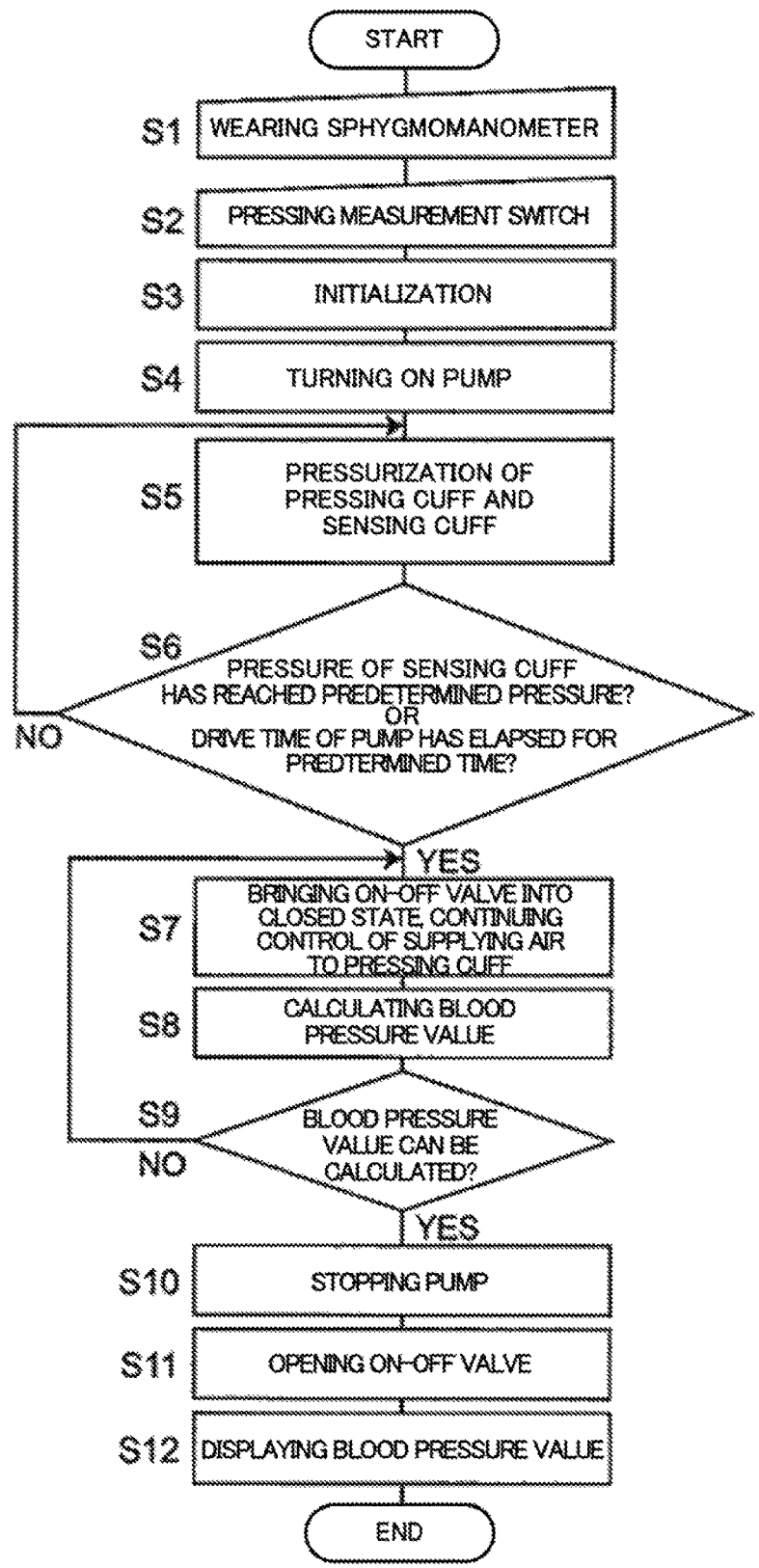
FIG. 11 is a diagram showing an operation flow when a user performs a blood-pressure measurement method of an embodiment to measure a blood pressure with the sphygmomanometer.

FIG. 11 shows an operation flow when the user performs a blood-pressure measurement method of an embodiment to measure a blood pressure with the sphygmomanometer 1.

As shown in step S1 of FIG. 11, the user wears the sphygmomanometer 1 on the left wrist 90 that is a measurement site. At the time of wearing, as shown in FIG. 13A, the user first wears the cuff structure 20 on the left wrist 90 by using a right hand 99 (step S21 of FIG. 12). The cuff structure 20 is curved along the circumferential direction Y of the left wrist 90 due to the curler 24 in the natural state. Therefore, in this example, the user fits the cuff structure 20 onto the outer circumferential surface of the left wrist 90 by using the hand (the right hand 99 in this example) on the right side of the body, i.e., on the side opposite to the left side of the body to which the left wrist 90 belongs, and can thereby easily wear the cuff structure 20 on the left wrist 90. While the cuff structure 20 is worn on the left wrist 90, the cuff structure 20 grips the left wrist 90 even when the user releases the right hand 99 from the cuff structure 20, so that the cuff structure 20 (as well as the belt 2 and the main body 10) hardly drops off.

Subsequently, as shown in FIG. 13B, the user uses the right hand 99 to bring the left wrist 90 and the cuff structure 20 into a state of being wrapped with the belt 2 together. Specifically, a portion leading to the tip portion 4f of the second belt part 4 is passed through the frame-shaped body 5A of the buckle 5 of the first belt part 3, and the prong 5B of the buckle 5 is then inserted into any one of the multiple small holes 4w, 4w . . . of the second belt part 4. Consequently, as shown in FIG. 13C, the first belt part 3 and the second belt part 4 are fastened (step S22 of FIG. 12). As a result, the left wrist 90 is wrapped with the belt 2 extending from the main body 10, and the strap-shaped cuff structure 20 having the one end 20f attached to the main body 10 is disposed on the inner circumferential side closer to the left wrist 90 than the belt 2.

In the sphygmomanometer 1, the cuff structure 20 can be separated from the inner circumferential surfaces 3a, 4a of the belt 2, and the other end 20e on the side opposite to the one end 20f of the cuff structure 20 is a free end. Therefore, when the first belt part 3 and the second belt part 4 are fastened, the cuff structure 20 receives an inward force from the belt 2, and the cuff structure 20 may slide or deform exactly along the outer circumferential surface of the left wrist 90. As a result, in the worn state, the cuff structure 20 and the belt 2 are brought substantially into close contact with the outer circumferential surface of the left wrist 90 in this order, i.e., a state of wrapping the left wrist 90 in a strap shape as a whole. In this way, the sphygmomanometer 1 may easily be worn on the left wrist 90.

Figure 14:
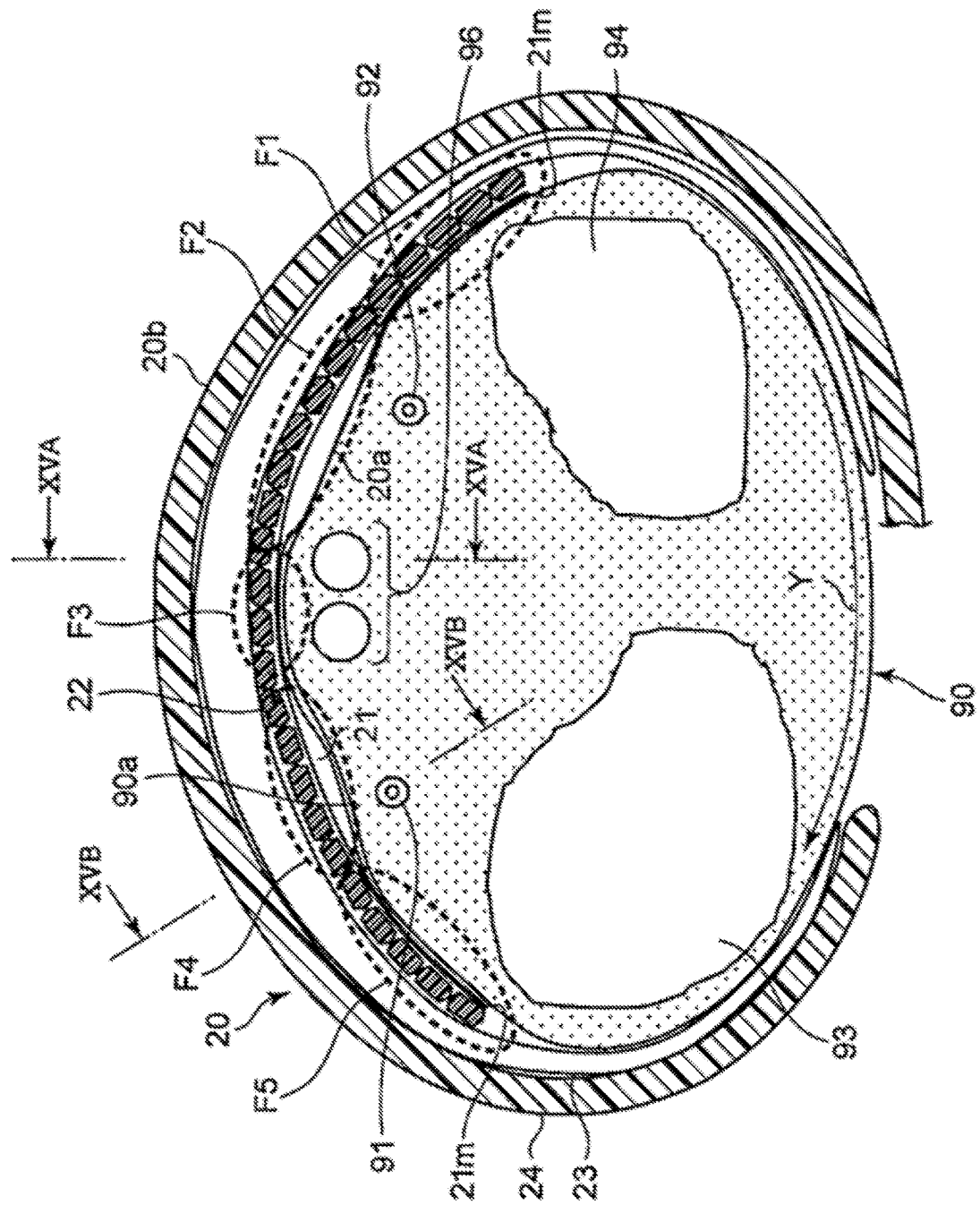
FIG. 14 is a view showing a cross section perpendicular to the left wrist while the sphygmomanometer is worn on the left wrist of the user.

Specifically, as shown in FIG. 14, in this worn state, the bag-shaped pressing cuff 23 extends along the circumferential direction Y of the left wrist 90 on the inner circumferential side of the curler 24 included in the cuff structure 20. The bag-shaped sensing cuff 21 included in the cuff structure 20 is disposed on the inner circumferential side relative to the pressing cuff 23 and in contact with the left wrist 90 and extends in the circumferential direction Y to cross an artery-passing portion 90a of the left wrist 90. Furthermore, the back plate 22 included in the cuff structure 20 is interposed between the pressing cuff 23 and the sensing cuff 21 and extends along the circumferential direction Y of the left wrist 90. In FIG. 14, the main body 10 and the belt 2 are not shown. In FIG. 14, a radius 93, an ulna 94, a radial artery 91, an ulnar artery 92, and tendons 96 of the left wrist 90 are shown.

Subsequently, when the user presses the measurement switch 52A of the operation part 52 disposed on the main body 10 (step S2 of FIG. 11), the CPU 100 initializes a processing memory area (step S3 of FIG. 11). The CPU 100 turns off the pump 30 via the pump drive circuit 35, opens the exhaust valve built in the pump 30, and maintains the on-off valve 33 in the opened state to exhaust the air in the pressing cuff 23 and the sensing cuff 21. Subsequently, control is provided to adjust 0 mmHg of the first pressure sensor 31 and the second pressure sensor 32.

The CPU 100 then functions as a pressurization control part and a fluid storage control part to turn on the pump 30 via the pump drive circuit 35 (step S4 of FIG. 11), maintains the on-off valve 33 in the opened state, and starts pressurization of the pressing cuff 23 and the sensing cuff 21 (step S5 of FIG. 11). In a pressurization process, the pump 30 is driven via the pump drive circuit 35 while the pressures of the pressing cuff 23 and the sensing cuff 21 are monitored by the first pressure sensor 31 and the second pressure sensor 32, respectively. As a result, controls are provided to respectively send air to the pressing cuff 23 through the first flow path (the first flow-path forming member 390 and the flexible tube 39) and to the sensing cuff 21 through the second flow path (the second flow-path forming member 380 and the flexible tube 38).

At step S6 of FIG. 11, the CPU 100 then functions as the fluid storage control part to determine whether the pressure of the sensing cuff 21 has reached a predetermined pressure (15 mmHg in this example) or whether the drive time of the pump 30 has elapsed for a predetermined time (three seconds in this example). The reason for making this determination is to confirm whether an appropriate amount of air is stored in the sensing cuff 21. In the case of NO at step S6 of FIG. 11, the CPU 100 waits until the pressure of the sensing cuff 21 reaches a predetermined pressure or the drive time of the pump 30 elapses for a predetermined time. An amount of the pressure-transmitting fluid stored in the sensing cuff 21 considered as the "appropriate amount" will be described later.

Figure 16:
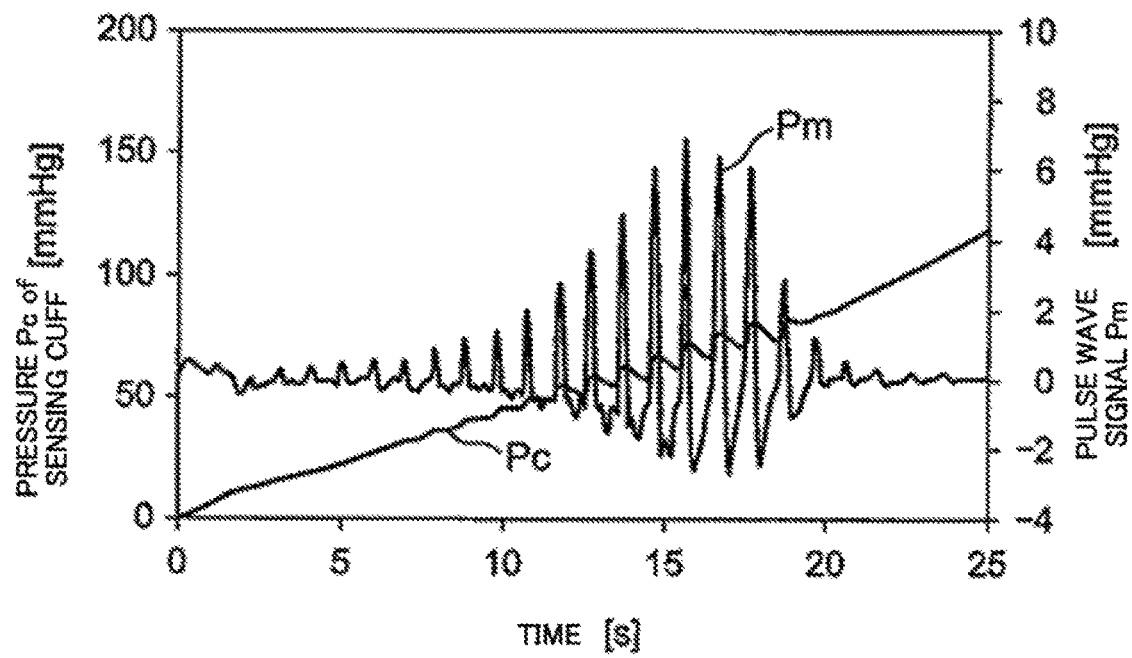
FIG. 16 is a view exemplarily showing a pressure Pc and a pulse wave signal Pm of a sensing cuff detected by a second pressure sensor mounted on the main body.

In the case of YES at step S6 of FIG. 11, it is determined that the appropriate amount of air is stored in the sensing cuff 21. At step S7 of FIG. 11, the CPU 100 then functions as the pressurization control part, brings the on-off valve 33 into the closed state, and continues a control of supplying air from the pump 30 through the first flow path to the pressing cuff 23. As a result, the pressing cuff 23 is inflated, and a pressure is gradually applied to compress the left wrist 90. At this point, the back plate 22 transmits the pressing force from the pressing cuff 23 to the sensing cuff 21. The sensing cuff 21 compresses the left wrist 90 (including the artery-passing portion 90a). In this pressurization process, to calculate a blood pressure value, the CPU 100 monitors a pressure Pc of the sensing cuff 21, i.e., the pressure of the artery-passing portion 90a of the left wrist 90, by the second pressure sensor 32, to acquire a pulse wave signal Pm as a variation component. FIG. 16 exemplarily shows the pressure Pc of the sensing cuff 21 and a waveform of the pulse wave signal Pm acquired in this pressurization process.

Figure 15A:
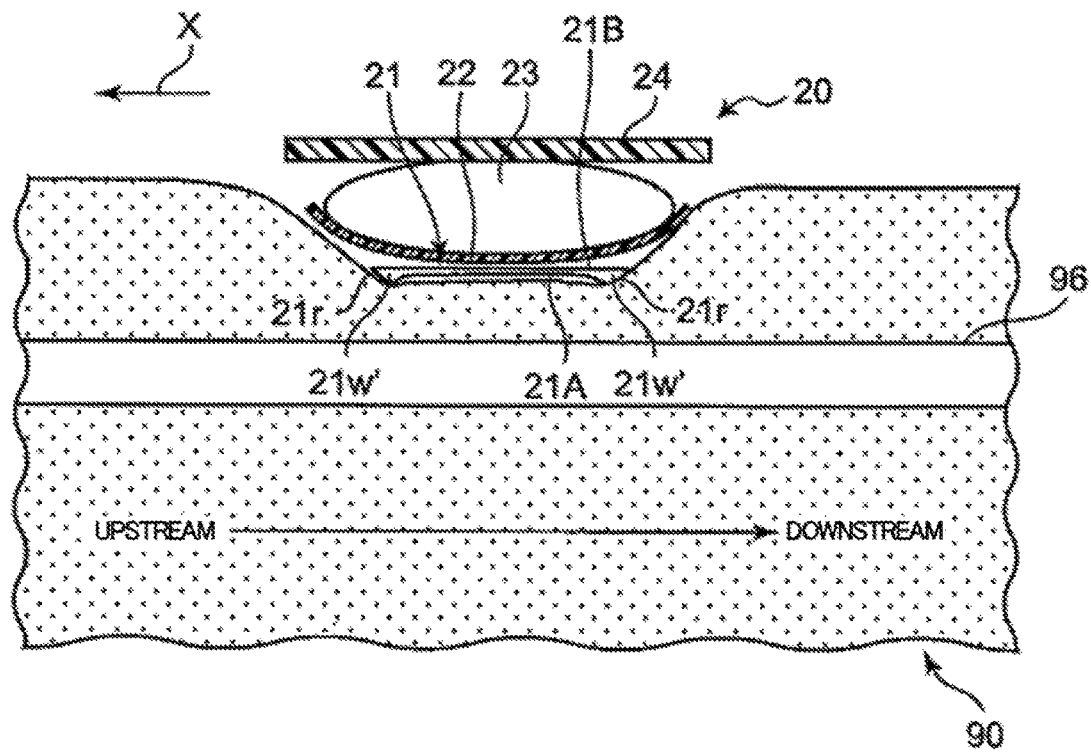
FIG. 15A is a view showing a cross section (corresponding to a cross section taken along a line XVA-XVA of FIG. 14 as viewed in a direction of arrows) of a portion through which a tendon of the left wrist passes in a pressurized state.
Figure 15B:
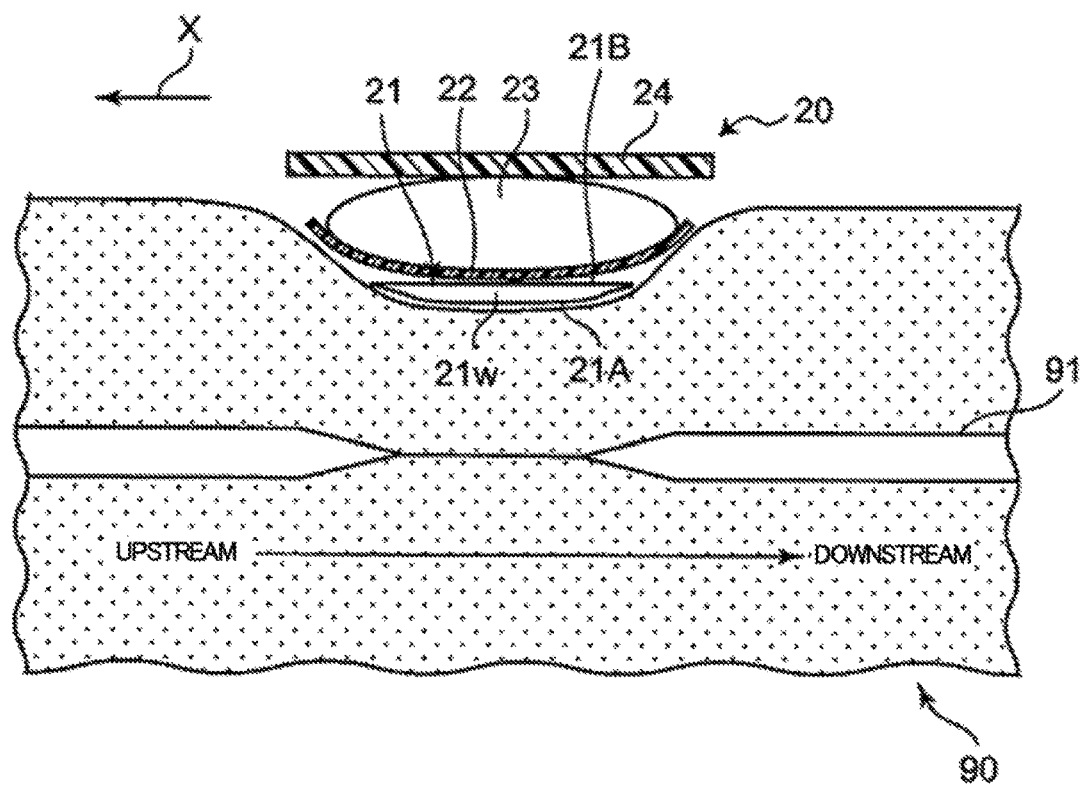
FIG. 15B is a view showing a cross section (corresponding to a cross section taken along a line XVB-XVB of FIG. 14 as viewed in a direction of arrows) of a portion through which the radial artery of the left wrist passes in the pressurized state.

FIGS. 15A and 15B schematically shows a cross section along the longitudinal direction of the left wrist 90 (corresponding to the width direction X of the cuff) in a pressurized state when an appropriate amount of air is stored in the sensing cuff 21 and the on/off valve 33 is closed. FIG. 15A shows a cross section (corresponding to a cross section taken along a line XVA-XVA of FIG. 14 as viewed in a direction of arrows) of a portion through which the tendon 96 of the left wrist 90 passes. On the other hand, FIG. 15B shows a cross section (corresponding to a cross section taken along a line XVB-XVB of FIG. 14 as viewed in a direction of arrows) of a portion through which the radial artery 91 of the left wrist 90 passes. As shown in FIG. 15B, a portion of the left wrist 90 having the radial artery 91 passing therethrough is relatively soft, so that a gap 21w with air present therein remains between the first sheet 21A and the second sheet 21B of the sensing cuff 21. Therefore, the portion of the sensing cuff 21 facing the radial artery 91 can reflect the pressure of the artery-passing portion 90a of the left wrist 90. On the other hand, as shown in FIG. 15A, a portion of the left wrist 90 having the tendon 96 passing therethrough is relatively hard, so that the first sheet 21A and the second sheet 21B are in contact with each other in a portion corresponding to substantially the center in the width direction X of the sensing cuff 21. However, the sensing cuff 21 is provided with the sags 21r, 21r extending along the longitudinal direction Y (corresponding to the circumferential direction of the left wrist 90) as described above at positions leading to the edge portions 21m, 21m on both sides in the width direction X, so that gaps 21w', 21w' with air present therein remain along the longitudinal direction Y. Consequently, the air stored in the sensing cuff 21 can flow along the longitudinal direction Y of the sensing cuff 21 through the gaps 21w', 21w'. Therefore, the sensing cuff 21 can successfully transmit the pressure applied to the artery-passing portion 90a of the left wrist 90 as the pressure of air (pressure-transmitting fluid) to the second pressure sensor 32 in the main body 10.

At step S8 of FIG. 11, the CPU 100 then functions as a blood-pressure calculating part and attempts to calculate a blood pressure value (systolic blood pressure SBP and diastolic blood pressure DBP) based on the pulse wave signal Pm acquired at this point by applying a known algorithm with the oscillometric method.

At this point, when the blood pressure value cannot yet be calculated because of insufficient data (NO at step S9), the processes of steps S7 to S9 are repeated as long as the cuff pressure process has not reached an upper limit pressure (predetermined for safety as, e.g., 300 mmHg).

When the blood pressure value is calculated in this way (YES at step S9), the CPU 100 stops the pump 30 (step S10) and opens the on-off valve 33 (step S11) to provide control of exhausting the air inside the pressure cuff 23 and the sensing cuff 21. Lastly, the measurement result of the blood pressure value is displayed on the display 50 (step S12).

The blood pressure calculation may be performed in a depressurization process rather than the pressurization process of the pressing cuff 23.

As described above, in the sphygmomanometer 1, air is stored in the sensing cuff 21 each time the blood pressure is measured, and the second pressure sensor 32 detects the pressure Pc of the sensing cuff 21, i.e., the pressure of the artery-passing portion 90a of the left wrist 90 itself, separately from the pressing cuff 23. Therefore, even if the pressing cuff 23 is largely inflated in the thickness direction and causes a compression loss at the time of pressurization as a result of setting a small dimension (e.g., about 25 mm) in the width direction X for the belt 2 and the cuff structure 20 (collectively referred to simply as a "cuff" as appropriate), the blood pressure can accurately be measured. In the worn state, the sensing cuff 21 extends in the circumferential direction Y to cross the artery-passing portion 90a of the left wrist 90. Therefore, even if the user actually wears the sphygmomanometer 1 on the left wrist 90 and the cuff is positionally displaced to some extent along with the main body 10 in the circumferential direction Y of the left wrist 90, the sensing cuff 21 does not fall outside the arterial passing portion 90a of the left wrist 90. Therefore, the blood pressure measurement value can be prevented from varying relative to the actual blood pressure, and consequently, the blood pressure can accurately be measured.

In the above example, air is stored as the pressure-transmitting fluid in the sensing cuff 21 each time the blood pressure is measured, and the air is exhausted after the measurement is completed; however, the present invention is not limited thereto. At a manufacturing stage of the sphygmomanometer 1, a pressure-transmitting fluid may be stored and sealed in the sensing cuff 21.

(Appropriate Amount of Pressure-Transmitting Fluid Stored in Sensing Cuff)

As shown in FIG. 14, the sensing cuff 21 is brought substantially into close contact with the outer circumferential surface of the left wrist 90 in the worn state, and in this state, the sensing cuff 21 can be roughly divided into five regions. The five regions are a region F1 corresponding to the ulna 94, a region F2 corresponding to the ulnar artery 92, a region F3 corresponding to the tendons, a region corresponding to the radial artery 91, and a region F5 corresponding to the radius 93 indicated by dotted ellipses in Fig. F4. Among these regions, the region F1 corresponding to the ulna 94, the region F3 corresponding to the tendons, and the region F4 corresponding to the radial artery 91 are regions corresponding to hard portions having the ulna 94, the tendons 96, and the radius 93, respectively, in the measurement site. The region F2 corresponding to the ulnar artery 92 and the region F4 corresponding to the radial artery 91 are regions corresponding to soft portions having the ulnar artery 92 and the radial artery 91, respectively, in the measurement site.

Assuming that the fluid is stored to such an extent that the sensing cuff 21 is inflated in all of the region F1, the region F2, the region F3, the region F4, and the region F5, when the sensing cuff 21 is pressed against the wrist, a repulsive force from all the regions is detected as the internal pressure of the sensing cuff 21 by the second pressure sensor 32, and the blood pressure value is calculated. However, since the regions F1, F3, and F5 are regions corresponding to the hard portions having the ulna 94, the tendons 96, and the radius 93, respectively, the repulsive force from these hard portions to the pressing force becomes higher than the repulsive force from the soft portions in the vicinities of the ulnar artery 92 and the radial artery 91. Consequently, the internal pressure of the sensing cuff 21 generally becomes higher than the pressure in the vicinities of the ulnar artery 92 and the radial artery 91, and the error of the blood pressure value becomes larger. The amount of the fluid stored in the sensing cuff 21 is also related to generation of tension in the first sheet 21A and the second sheet 213 constituting the sensing cuff 21, and when the amount of the fluid is larger, the tension increases, and the internal pressure of the sensing cuff 21 becomes higher, so that the error of the blood pressure value becomes larger also in this case. As described above, when the fluid is stored in the region F1, the region F3, and the region F5, the internal pressure becomes higher due to the influence of the repulsive force and the tension, and the error of the blood pressure value becomes larger.

However, as shown in FIG. 14, if the fluid is supplied such that the first sheet 21A and the second sheet 213 are in contact with each other in the region F1, the region F3, and the region F5 while the first sheet 21A and the second sheet 21B are separated from each other in the region F2 and the region F4, the influence from the hard portions described above disappears. Therefore, in the case that the amount of fluid is at this level, when the sensing cuff 21 is pressed against the wrist, the fluid does not exist in the region F1, the region F3, and the region F5 corresponding to the hard portions described above (or the fluid escapes if existing), and the fluid is stored in the region F2 and the region F4 corresponding to the two arteries, i.e., the radial artery 91 and the ulnar artery 92. Moreover, in the sphygmomanometer 1, the sensing cuff 21 is provided with the sags 21r, 21r extending along the longitudinal direction Y (corresponding to the circumferential direction of the left wrist 90) as shown in FIG. 15A at positions leading to the edge portions 21m, 21m on both sides in the width direction X, so that gaps 21w', 21w' remain along the longitudinal direction Y. As a result, in the region F1, the region F3, and the region F5, the fluid stored in the sensing cuff 21 flows through the gaps 21w', 21w' to the region F2 and the region F3, and the fluid is stored in the region F2 and the region F3. Although the first sheet 21A and the second sheet 21B shown in FIG. 15A are slightly separated for facilitating understanding, the first sheet 21A and the second sheet 21B are actually in contact with each other.

As described above, if the amount of the fluid is as shown in FIG. 14, the fluid does not exist in the region F1, the region F3, and the region F5, and therefore, the repulsive force from the ulna 94, the tendons 96, and the radius 93 does not contribute to the internal pressure of the sensing cuff 21. Additionally, since the fluid does not exist in these regions, the tension due to the fluid is not generated in the first sheet 21A and the second sheet 21E.

On the other hand, in the region F2 and the region F4 corresponding to the soft portions having the two arteries, i.e., the radial artery 91 and the ulnar artery 92, the fluid is stored such that the first sheet 21A and the second sheet 21B of the sensing cuff 21 are separated from each other. Therefore, the pressure around the radial artery 91 and the ulnar artery 92 is detected as the internal pressure of the sensing cuff 21. As described above, by setting the amount of fluid as shown in FIG. 14, the internal pressure of the sensing cuff 21 is exclusively detected from the region F2 and the region F4 corresponding to the soft portions having the two arteries, i.e., the radial artery 91 and the ulnar artery 92, and therefore, the internal pressure of the sensing cuff 21 can be made equal to the pressure around the radial artery 91 and the ulnar artery 92, so that the error of the blood pressure value is reduced.

However, since the area of the soft portions having the two arteries, i.e., the radial artery 91 and the ulnar artery 92, differs depending on a user, the present inventor conducted an experiment to calculate a blood-pressure measurement error (average value) when the amount of the fluid is variably set for various users. The dimensions of the parts of the sphygmomanometer 1 used in the experiment are as described above. Particularly, describing the sensing cuff 21 again, the dimension in the width direction X (excluding welded edge portions on both sides) is set to W4=15 mm, and the dimension in the longitudinal direction Y is set to L4=110 mm.

Figure 17:
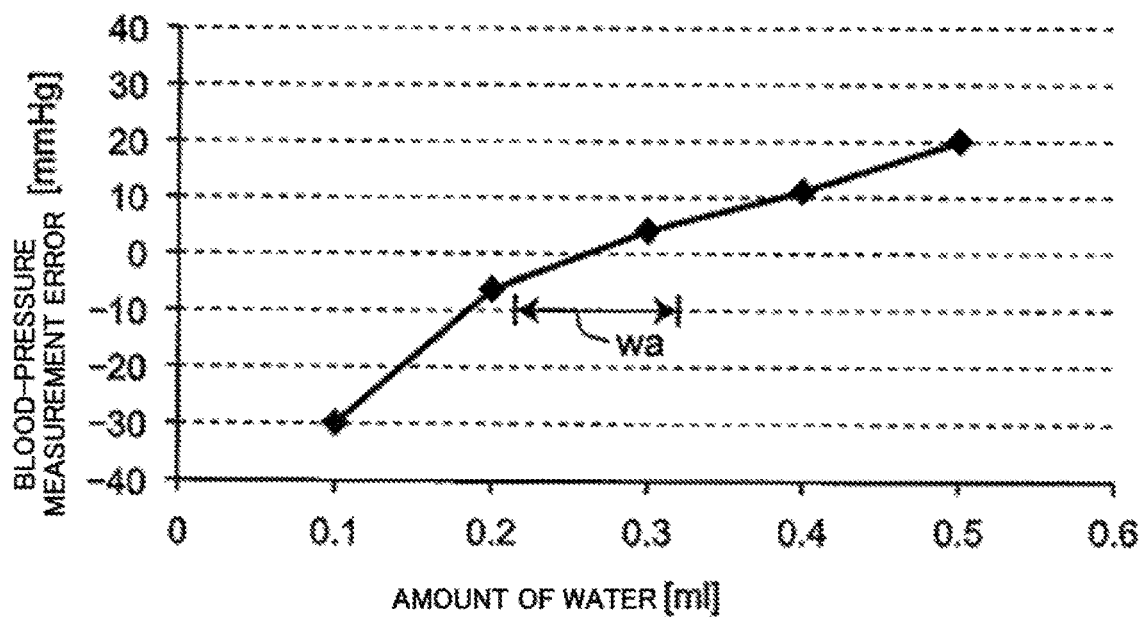
FIG. 17 is a view showing a blood-pressure measurement error when water is used as a pressure-transmitting fluid stored in the sensing cuff and an amount of the water stored in the sensing cuff is variably set.

FIG. 17 shows a blood-pressure measurement error (average value) when water is used as the pressure-transmitting fluid stored in the sensing cuff 21 and an amount of water stored in the sensing cuff 21 is variably set. The blood-pressure measurement error means a difference acquired by subtracting a blood pressure value (systolic blood pressure SBP) measured by a standard (correct) sphygmomanometer (this is called "reference blood pressure value") from a blood pressure value (systolic blood pressure SBP) measured by the sphygmomanometer 1 for a certain user (subject). This is represented as follows:

(blood-pressure measurement error)=(blood pressure value measured by the sphygmomanometer 1)−(reference blood pressure value). As can be seen from FIG. 17, when the amount of water stored in the sensing cuff 21 is within a range wa of 0.26 ml±0.05 ml, the blood-pressure measurement error is within ±5 mmHg, so that the amount is considered as an appropriate amount.

In FIG. 17, when the amount of water exceeds the appropriate amount range wa, the blood-pressure measurement error becomes larger on the positive side. A possible reason is that since water is stored in the region F1, the region F3, and the region F5 corresponding to the hard portions described above in the cross section shown in FIG. 14, the internal pressure of these regions is made higher due to the influence of the repulsive force and the tension described above, resulting in the increased internal pressure of the sensing cuff 21. Another reason is that since portions having the radial artery 91 and the ulnar artery 92 passing therethrough are relatively soft, the water present more than necessary in these portions expands the sensing cuff 21 and raises the internal pressure of the sensing cuff 21 due to tension of the expansion. In FIG. 17, when the amount of water falls below the appropriate range wa, the blood-pressure measurement error becomes larger on the negative side. The possible reason is that since the amount of water stored in the sensing cuff 21 is too small, the water (pressure-transmitting fluid) does not completely delivered to the region F2 and the region F4 corresponding to the soft portions having the two arteries, i.e., the radial artery 91 and the ulnar artery 92, which makes it unable to detect the pressure.

The present inventor conducted the same experiment for multiple users and discovered that an amount of fluid within the range wa can achieve the blood-pressure measurement error within ±5 mmHg, bring the first sheet 21A and the second sheet 21B into contact with each other in the region F1, the region F3, and the region F5, and separate the first sheet 21A and the second sheet 21B from each other in the region F2 and the region F4. Additionally, the present inventor discovered that at the step shown in step S6 of FIG. 11, the fluid can be supplied in an amount within the range wa when the pressure of the sensing cuff 21 reaches 15 mmHg or the drive time of the pump 30 is set to three seconds. The pressure of 15 mmHg and the drive time of three seconds are merely examples, and the present invention is not limited to these values.

Obviously, the appropriate amount of the pressure-transmitting fluid stored in the sensing cuff 21 depends on the size etc. of the sensing cuff 21.

In this embodiment, based on the results of the experiments, in the pressurization process of the sensing cuff 21 shown in step S6 of FIG. 11, the pump 30 is driven until the pressure of the sensing cuff 21 reaches 15 mmHg, or the drive time of the pump 30 is set to three seconds, to supply an appropriate amount of fluid, i.e., an amount of fluid within the range wa, to the sensing cuff 21. In other words, in the present invention, the fluid is supplied such that the first sheet 21A and the second sheet 21B are brought into contact with each other in the region F1, the region F3, and the region F5 corresponding to the hard portions having the ulna 94, the tendons 96, and the radius 93 while the first sheet 21A and the second sheet 21B are separated from each other in the region F2 and the region F4 corresponding to the soft portions having the two arteries, i.e., the radial artery 91 and the ulnar artery 92. According to the present invention, the internal pressure of the sensing cuff 21 can be made equal to the pressure around the radial artery 91 and the ulnar artery 92, so that the error of the blood pressure value is reduced. Therefore, a blood pressure measurement value can be prevented from varying relative to an actual blood pressure, and consequently, the blood pressure can accurately be measured.

(Verification Result)

Figure 18:
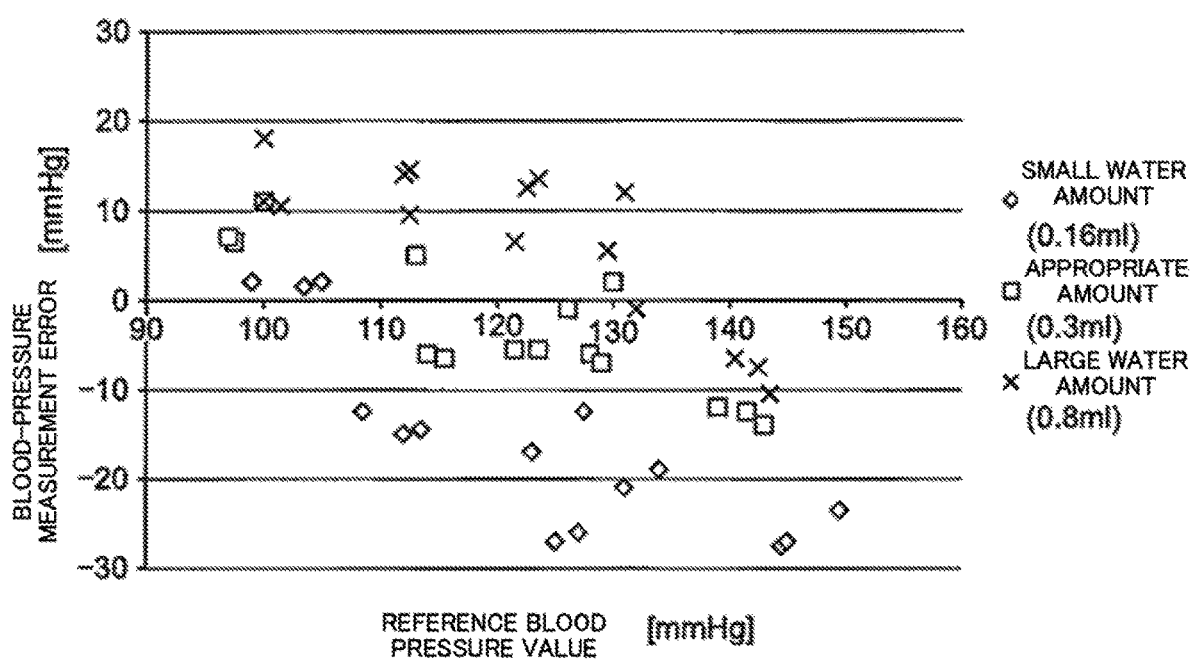
FIG. 18 is a scatter diagram of a relationship between a reference blood pressure value and a blood-pressure measurement error when the amount of the water stored in the sensing cuff is variably set to "small water amount"=0.16 ml, "appropriate amount"=0.3 ml, "large water amount"=0.8 ml for multiple users.

A scatter diagram of FIG. 18 shows a relationship between the reference blood pressure value and the blood-pressure measurement error when the amount of the pressure-transmitting fluid stored in the sensing cuff 21 is variably set to "small water amount"=0.16 ml, "appropriate amount"=0.3 ml, "large water amount"=0.8 ml for multiple users (in this example, measurement is performed three times for each of five subjects with the systolic blood pressure SBP of 97 mmHg to 149 mmHg). When the amount of water is the "appropriate amount", the blood-pressure measurement error is reduced for the multiple users as indicated by square marks in the figure. On the other hand, in the case of the "large water amount", the blood-pressure measurement error becomes larger on the positive side for the multiple users as indicated by cross marks in the figure. In the case of the "small water amount", the blood-pressure measurement error becomes larger on the negative side for the multiple users as indicated by diamond marks in the figure.

This verification result can be considered as giving confirmation to the fact that the sphygmomanometer 1 of the present invention can accurately measure the blood pressure even when the blood pressure is measured by using the bag-shaped sensing cuff on the measurement site that is the wrist where the tendons 96, the radius 93, and the ulna 94 exist.

Particularly, when multiple users each actually wear the sphygmomanometer 1 on the left wrist 90 and measure the blood pressure, the area of the soft portion having the two arteries, i.e., the radial artery 91 and the ulnar artery 92, is different depending on a user. In the verification result of FIG. 18, when the amount of water is appropriate, the blood-pressure measurement errors are suppressed for the multiple users. Therefore, the verification result can be considered as giving confirmation to the fact that this sphygmomanometer 1 can accurately measure the blood pressure even when the area of the soft portion having the two arteries, i.e., the radial artery 91 and the ulnar artery 92, is different.

In the embodiment described above, the sensing cuff 21 is in direct contact with the left wrist 90 that is the measurement site in the described example; however, the present invention is not limited thereto. The sensing cuff 21 may be in indirect contact with the left wrist 90 via another member (e.g., a cover member).

In the embodiment described above, the left wrist 90 is the measurement site on which the sphygmomanometer is worn. However, the present invention is not limited thereto. The sphygmomanometer of the present invention may be configured to be optically symmetric to the sphygmomanometer 1 shown in FIGS. 1 and 2 and may be worn on the right wrist. The measurement site may be a site other than the wrist, such as an upper arm and a lower limb.

The embodiment described above is configured such that the main body 10 and the belt 2 are formed separately from each other and that the belt 2 is attached to the main body 10. However, the present invention is not limited thereto. The main body 10 and the belt 2 may integrally be molded.

In the embodiment described above, the first belt part 3 and the second belt part 4 of the belt 2 are fastened or released by the buckle 5. However, the present invention is not limited thereto. For example, the first belt part 3 and the second belt part 4 may be coupled to each other via an openable/closable triple-folding buckle.

In the embodiment described above, the cuff structure 20 includes the curler 24 in the described example. However, the present invention is not limited thereto, and the curler 24 may not be included. In this case, the belt 2 may be formed of one strap-shaped body; the pressing cuff 23 may be disposed along the inner circumferential surface of the strap-shaped body; the back plate 22 may be disposed along the inner circumferential surface of the pressing cuff 23; and the sensing cuff 21 may be disposed along the inner circumferential surface of the back plate 22. In this case, the belt 2 described above, the pressing cuff 23, and the back plate 22 function as pressing members capable of generating a pressing force toward the wrist, and the wrist is compressed via the sensing cuff 21 by these pressing members. Regarding the belt 2, for example, the back lid 10C of the main body 10 may include an openable/closable triple-folding buckle, and the end portions of the belt 2 may be coupled to the triple-folding buckle.

In the embodiment described above, the pump 30 is driven until the pressure of the sensing cuff 21 reaches 15 mmHg, or the drive time of the pump 30 is set to three seconds, in the pressurization process of the sensing cuff 21 shown in step S6 of FIG. 11. However, the present invention is not limited to this example, and the pump 30 may be driven until the pressure of the sensing cuff 21 reaches, for example, 5 mmHg, and after the fluid is filled in the sensing cuff 21, an amount of the fluid in the sensing cuff 21 may gradually be optimized. Alternatively, after air is first filled in the sensing cuff 21 by the pump 30 until reaching a relatively high pressure, for example, 30 mmHg, the pump 30 may be stopped and the exhaust valve may be opened to reduce the pressure of the sensing cuff 21 to a relatively low pressure, for example, 15 mmHg, and the exhaust valve may be closed to optimize the fluid volume in the sensing cuff 21. In this case, the exhaust valve may be disposed separately from the pump 30, and a valve drive circuit driving the exhaust valve may be disposed to be controllable by the CPU 100.

In the embodiment described above, the belt 2, the curler 24, the pressing cuff 23, and the back plate 22 are described as examples of the pressing member; however, the present invention is not limited thereto, and the pressing member may mechanically extend in the thickness direction.

In the embodiment described above, the pump 30 is included in the main body 10 in the described example; however, the present invention is not limited thereto, and a cuff including the belt 2 and the cuff structure 20 and a main body placed on a table may be included, and the pump may be included in this main body. In this case, the cuff and the main body may be connected via an elongated tube, and a fluid may be supplied from the main body to the cuff.

In the embodiment described above, the CPU 100 mounted on the sphygmomanometer 1 functions as the fluid storage control part, the pressurization control part, and the blood-pressure calculating part to perform the blood pressure measurement (the operation flow of FIG. 11). However, the present invention is not limited thereto. For example, a substantial computer device such as a smartphone disposed outside the sphygmomanometer 1 may function as the fluid storage control part, the pressurization control part, and the blood-pressure calculating part to cause the sphygmomanometer 1 to perform the blood pressure measurement (the operation flow of FIG. 11) via a network 900.

As is described above, a sphygmomanometer of the present disclosure is a sphygmomanometer comprising:

a pressing member disposed to wrap a wrist that is a measurement site in a circumferential direction and generating a pressing force toward the wrist;

a sensing cuff that includes a second sheet disposed to face an inner circumferential surface of the pressing member and a first sheet facing the second sheet, that is formed into a bag shape for storing a pressure-transmitting fluid with circumferential edge portions of the first and second sheets brought into close contact with each other, that extends in the circumferential direction to cross an artery-passing portion of the wrist, and that allows entire areas surrounded by the circumferential edge portions of the first and second sheets to separate from each other;

a pressurization control part providing a control of compressing the wrist by the pressing member via the sensing cuff;

a fluid storage control part providing a control of supplying and storing the pressure-transmitting fluid into the sensing cuff in a worn state in which the pressing member and the sensing cuff are worn on the wrist; and a blood-pressure calculating part calculating a blood pressure based on a pressure of the pressure-transmitting fluid stored in the sensing cuff, wherein the fluid storage control part supplies the fluid in the worn state such that the first and second sheets are in contact with each other in a region corresponding to an ulna, a region corresponding to a radius, and a region corresponding to a tendon while the first and second sheets are separated from each other in regions corresponding to two arteries that are radial and ulnar arteries, and wherein the pressurization control part provides the control of compressing the wrist by the pressing member via the sensing cuff in this state.

The pressurizing and pressure-transmitting "fluid" is typically air or may be another gas or liquid. The "pressure-transmitting fluid" may be stored in the sensing cuff at a manufacturing stage of the sphygmomanometer or may be stored in the sensing cuff and discharged from the sensing cuff each time a blood pressure is measured.

The "inner circumferential surface" of the pressing member refers to the surface on the inner circumferential side in the worn state in which the measurement site is wrapped.

The sphygmomanometer of the present disclosure is worn on the wrist with the pressing member wrapping the wrist that is the measurement site in the circumferential direction and with the sensing cuff disposed to face the inner circumferential surface of the pressing member. In this worn state, the bag-shaped sensing cuff is disposed on the inner circumferential side relative to the pressing cuff to face the wrist and extends in the circumferential direction to cross the artery-passing portion of the wrist.

At the time of blood pressure measurement, for example, first, the fluid storage control part supplies the fluid in the worn state such that the first and second sheets are in contact with each other in a region corresponding to an ulna, a region corresponding to a radius, and a region corresponding to a tendon while the first and second sheets are separated from each other in regions corresponding to two arteries that are radial and ulnar arteries. In that state, the pressurization control part provides the control of compressing the wrist by the pressing member via the sensing cuff. Consequently, the sensing cuff compresses the wrist (including the artery-passing portion). In a pressurization process or a decompression process of the pressing member, the blood-pressure calculating part calculates a blood pressure based on a pressure of the pressure-transmitting fluid stored in the sensing cuff (the oscillometric method).

In this sphygmomanometer, the sensing cuff detects the pressure itself applied to the artery-passing portion of the wrist. In this case, the amount of the fluid supplied to the sensing cuff is controlled by the fluid storage control part such that, in the worn state, the first and second sheets constituting the sensing cuff are in contact with each other in a region corresponding to an ulna, a region corresponding to a radius, and a region corresponding to a tendon while the first and second sheets are separated from each other in regions corresponding to two arteries that are radial and ulnar arteries.

Specifically, the amount of the fluid is controlled to such an amount that the fluid does not exist in the regions corresponding to the hard portions having the ulna, the radius and the tendon while the fluid is stored in the regions corresponding to the two arteries, i.e., the radial artery and the ulnar artery. Therefore, in the regions of the sensing cuff corresponding to these hard portions, the repulsive force from the ulna, the tendon, and the radius does not contribute to the internal pressure of the sensing cuff. On the other hand, in the regions corresponding to soft portions having two arteries, i.e., the radial artery and the ulnar artery, the fluid is stored such that the first and second sheets of the sensing cuff are separated from each other. Therefore, the pressure around the radial artery and the ulnar artery is detected as the internal pressure of the sensing cuff. As described above, the internal pressure of the sensing cuff is exclusively detected from the regions corresponding to the soft portions having the two arteries, i.e., the radial artery and the ulnar artery, and therefore, the internal pressure of the sensing cuff can be made equal to the pressure around the radial artery and the ulnar artery, so that an error of the blood pressure value is reduced. Therefore, a blood pressure measurement value can be prevented from varying relative to an actual blood pressure, and consequently, the blood pressure can accurately be measured.

In the sphygmomanometer, the fluid storage control part provides the control of supplying and storing the pressure-transmitting fluid into the sensing cuff in the worn state. Therefore, the pressure-transmitting fluid can be stored in the sensing cuff each time the blood pressure is measured. When the blood pressure measurement is completed, the pressure-transmitting fluid may be discharged from the sensing cuff.

In the sphygmomanometer of an embodiment, the sensing cuff is provided with sags extending along a longitudinal direction of the sensing cuff in a natural state at positions leading to edge portions on both sides of the first and second sheets in a width direction of the sensing cuff.

The sags of the first and second sheets of the sensing cuff may be formed, for example, when the circumferential edge portions of the first and second sheets are welded and brought into close contact with each other.

In the sphygmomanometer of the embodiment, the sags extending along the longitudinal direction of the sensing cuff are disposed in the natural state at positions leading to the edge portions on both sides of the first and second sheets in the width direction of the sensing cuff. Therefore, even when the first and second sheets of the sensing cuff are sandwiched between the pressing member and the wrist and brought into contact with each other during pressurization of the pressing member, gaps extending along the longitudinal direction of the sensing cuff (corresponding to the circumferential direction of the wrist) remain because of the sags at positions leading to the edge portions on both sides in the width direction of the sensing cuff. The amount of the fluid is controlled by the fluid storage control part to such an amount that, in the worn state, the first and second sheets constituting the sensing cuff are in contact with each other in the region corresponding to the ulna, the region corresponding to the radius, and the region corresponding to the tendon while the first and second sheets are separated from each other in the regions corresponding to the two arteries that are the radial and ulnar arteries. Consequently, the pressure-transmitting fluid supplied to the sensing cuff may flow from the region corresponding to the ulna, the region corresponding to the radius, and the region corresponding to the tendon through the gaps to the regions corresponding to the two arteries that are the radial and ulnar arteries. Therefore, the pressure applied to the artery-passing portion of the wrist can successfully be transmitted as the pressure of the pressure-transmitting fluid to the blood-pressure calculating part.

In the sphygmomanometer of an embodiment,
the pressing member includes
a belt to be worn to wrap the wrist in the circumferential direction,
a bag-shaped pressing cuff disposed to face an inner circumferential surface of the belt and extending along the circumferential direction of the wrist to receive a supply of a pressurizing fluid and compress the wrist, and
a back plate interposed between the pressing cuff and the sensing cuff and extending along the circumferential direction of the wrist to transmit a pressing force from the pressing cuff to the sensing cuff.

The sphygmomanometer is worn on the wrist with the belt wrapping the wrist in the circumferential direction and with the pressing cuff, the back plate, and the sensing cuff arranged in this order to face the inner circumferential surface of the belt. In this worn state, the pressing cuff extends along the circumferential direction of the wrist. The sensing cuff is disposed on the inner circumferential side relative to the pressing cuff to face the wrist and extends in the circumferential direction to cross the artery-passing portion of the wrist. Furthermore, the back plate is interposed between the pressing cuff and the sensing cuff and extends along the circumferential direction of the wrist. Therefore, a cuff of the sphygmomanometer can be formed into a strap shape as a whole, and the sphygmomanometer with good usability for the user can be provided.

The belt is desirably made of a material flexible in the thickness direction of this belt and substantially inelastic in the longitudinal direction of this belt (corresponding to the circumferential direction of the measurement site). As a result, the belt can easily wrap and bind the outer circumferential side described above at the time of wearing and can assist compression of the wrist at the time of blood pressure measurement.

The sphygmomanometer of an embodiment comprises
a main body equipped with a pump, and
the belt extends from the main body.

As used herein, a "belt" "extending from the main body" means that the main body and the belt may integrally be molded or that the main body and the belt may be formed separately from each other before attaching the belt to the main body. Regarding the belt itself, a first belt part extending from the main body to one side in one direction and the second belt part extending from the main body to the other side in in opposite direction may be fastened or released by a buckle or may be coupled by an openable/closable buckle.

This sphygmomanometer has the pump mounted on the main body and can easily be worn on the wrist by the belt extending from the main body. Therefore, the sphygmomanometer can be small-sized and integrally formed, and the sphygmomanometer can be carried, so that the sphygmomanometer with good usability for the user can be provided.

In the sphygmomanometer of an embodiment,
the pressing cuff, the back plate, and the sensing cuff constitute a cuff structure having a strap shape and one end attached to the main body, and
the cuff structure further includes a curler for keeping a shape of the cuff structure in a natural state curved along the circumferential direction of the wrist along an outer circumferential surface of the pressing cuff.

As used herein, the "curler" refers to a member typically made up of a resin plate having certain degrees of flexibility and hardness and having a shape curved along the circumferential direction surrounding the measurement site in the natural state.

The sphygmomanometer of the embodiment can easily be worn on the wrist. Specifically, at the time of wearing, first, the user wears the cuff structure on the wrist (e.g., the left wrist) (a first step of wearing). Since the cuff structure is curved along the circumferential direction of the wrist due to the curler in the natural state, the user fits the cuff structure onto an outer circumferential surface of the measurement site by using the hand (the right hand in this example) on the side opposite to the side of the body to which the wrist (the left wrist in this example) belongs, and can thereby easily wear the cuff structure on the wrist. While the cuff structure is worn on the wrist, the cuff structure grips the wrist even when the user releases the hand (the right hand in this example) from the cuff structure, so that the cuff structure (as well as the belt and the main body) hardly drops off. Subsequently, the user uses the hand (the right hand in this example) to bring the wrist and the cuff structure into a state of being wrapped with the belt together (a second step of wearing). In this way, the sphygmomanometer of the embodiment may easily be worn on the measurement site.

Since the cuff structure is not attached to the belt, the dimension in the longitudinal direction of the cuff structure (corresponding to the circumferential direction of the measurement site) can be set to an optimal dimension independently of the belt.

In the sphygmomanometer of an embodiment, a root portion on the main body side of the curler forming the one end of the cuff structure is sandwiched between a member disposed in the main body and a back lid of the main body, so that the one end of the cuff structure is attached to the main body.

In the sphygmomanometer of the embodiment, a root portion on the main body side of the curler forming the one end of the cuff structure is sandwiched between a member disposed in the main body and a back lid of the main body. As a result, the one end of the cuff structure is attached to the main body. Therefore, the one end of the cuff structure is reliably held by the main body. At the time of maintenance service, the cuff structure can be replaced for the main body independently of the belt by opening the back lid of the main body.

If the main body and the belt are formed separately from each other and the belt is configured to be attached to the main body, the belt can be replaced for the main body independently of the cuff structure at the time of maintenance service.

In the sphygmomanometer of an embodiment, the other end of the cuff structure on the side opposite to the one end is a free end.

In the sphygmomanometer of the embodiment, the other end of the cuff structure on the side opposite to the one end is a free end, and therefore, when the user brings the wrist and the cuff structure into a state of being wrapped with the belt together at the time of wearing (the second step of wearing), the cuff structure receives an inward force from the belt, and the cuff structure may slide or deform exactly along the outer circumferential surface of the wrist. As a result, in the worn state, the cuff structure and the belt are brought substantially into close contact with the outer circumferential surface of the measurement site in this order. Consequently, the blood pressure can accurately be measured.

In the sphygmomanometer of an embodiment,
the back plate extends in a strap shape beyond the length of the sensing cuff in the circumferential direction of the wrist, and
the back plate includes a plurality of grooves having V-shaped or U-shaped cross sections, extending in the width direction of the back plate, and parallelly separated from each other in the longitudinal direction of the back plate, which allows the back plate to curve along the circumferential direction.

In the sphygmomanometer of the embodiment, the back plate extends in a strap shape beyond the length of the sensing cuff in the circumferential direction of the wrist. Therefore, the back plate can transmit the pressing force from the pressing cuff to an entire area in the longitudinal direction of the sensing cuff (corresponding to the circumferential direction of the wrist). The back plate includes a plurality of grooves having V-shaped or U-shaped cross sections, extending in the width direction of the back plate, and parallelly separated from each other in the longitudinal direction of the back plate, which allows the back plate to curve along the circumferential direction. Therefore, when the user brings the wrist and the cuff structure into a state of being wrapped with the belt together at the time of wearing (the second step of wearing), the back plate does not prevent the cuff structure from curving along the circumferential direction of the wrist.

In the sphygmomanometer of an embodiment,
the main body is equipped with
a first flow path connecting the pump and the pressing cuff to allow a fluid to flow therebetween, and
a second flow path connecting the pump or the first flow path and the sensing cuff to allow a fluid to flow therebetween and having an on-off valve interposed therein,
in the worn state, the fluid storage control part brings the on-off valve into an opened state and supplies and stores the pressure-transmitting fluid from the pump or the first flow path through the second flow path into the sensing cuff, and
after the pressure-transmitting fluid is stored in the sensing cuff, the pressurization control part brings the on-off valve into a closed state and supplies the pressurizing fluid from the pump through the first flow path to the pressing cuff to compress the measurement site.

In the sphygmomanometer of the embodiment, the pressure-transmitting fluid can be supplied and stored into the sensing cuff with a simple configuration. Additionally, while the pressure-transmitting fluid is stored and enclosed in the sensing cuff, the pressurizing fluid can be supplied to the pressing cuff for pressurization.

In the sphygmomanometer of an embodiment,
the main body is equipped with the pressurization control part, the blood-pressure calculating part, and the fluid storage control part.

The sphygmomanometer of the embodiment may be small-sized and integrally formed. Therefore, the usability for the user is good.

In another aspect, the present disclosure provides a blood-pressure measurement method of measuring a blood pressure of a measurement site, including
a pressing member disposed to wrap a wrist that is the measurement site in a circumferential direction and generating a pressing force toward the wrist, and
a sensing cuff that includes a second sheet disposed to face an inner circumferential surface of the pressing member and a first sheet facing the second sheet, that is formed into a bag shape for storing a pressure-transmitting fluid with circumferential edge portions of the first and second sheets brought into close contact with each other, that extends in the circumferential direction to cross an artery-passing portion of the wrist, and that allows entire areas surrounded by the circumferential edge portions of the first and second sheets to separate from each other, wherein
in a worn state in which the pressing member and the sensing cuff are worn on the wrist, the fluid is supplied and stored into the sensing cuff such that the first and second sheets are in contact with each other in a region corresponding to an ulna, a region corresponding to a radius, and a region corresponding to a tendon while the first and second sheets are separated from each other in regions corresponding to two arteries that are radial and ulnar arteries, wherein
a control is provided in this state to compress the wrist by the pressing member via the sensing cuff, and wherein
a blood pressure is calculated based on a pressure of the pressure-transmitting fluid stored in the sensing cuff.

According to the blood-pressure measurement method of the present disclosure, at the time of blood pressure measurement, the fluid is supplied in the worn state such that the first and second sheets are in contact with each other in a region corresponding to an ulna, a region corresponding to a radius, and a region corresponding to a tendon while the first and second sheets are separated from each other in regions corresponding to two arteries that are radial and ulnar arteries. A control is provided in this state to compress the wrist by the pressing member via the sensing cuff. Consequently, the sensing cuff compresses the wrist (including the artery-passing portion). In a pressurization process or a decompression process of the pressing member, the blood-pressure calculating part calculates a blood pressure based on a pressure of the pressure-transmitting fluid stored in the sensing cuff (the oscillometric method).

In this method, the sensing cuff detects the pressure itself applied to the artery-passing portion of the wrist. In this case, the fluid is supplied to the sensing cuff in the worn state such that the first and second sheets constituting the sensing cuff are in contact with each other in a region corresponding to an ulna, a region corresponding to a radius, and a region corresponding to a tendon while the first and second sheets are separated from each other in regions corresponding to two arteries that are radial and ulnar arteries.

Specifically, the amount of the fluid is controlled to such an amount that the fluid does not exist in the regions corresponding to the hard portions having the ulna, the radius and the tendon while the fluid is stored in the regions corresponding to the two arteries, i.e., the radial artery and the ulnar artery. Therefore, in the regions of the sensing cuff corresponding to these hard portions, the repulsive force from the ulna, the tendon, and the radius does not contribute to the internal pressure of the sensing cuff. On the other hand, in the regions corresponding to soft portions having two arteries, i.e., the radial artery and the ulnar artery, the fluid is stored such that the first and second sheets of the sensing cuff are separated from each other. Therefore, the pressure around the radial artery and the ulnar artery is detected as the internal pressure of the sensing cuff. As described above, the internal pressure of the sensing cuff is exclusively detected from the regions corresponding to the soft portions having the two arteries, i.e., the radial artery and the ulnar artery, and therefore, the internal pressure of the sensing cuff can be made equal to the pressure around the radial artery and the ulnar artery, so that an error of the blood pressure value is reduced. Therefore, a blood pressure measurement value can be prevented from varying relative to an actual blood pressure, and consequently, the blood pressure can accurately be measured.

In another aspect, a device of the present disclosure is a device comprising: a blood-pressure measurement element, wherein the blood-pressure measurement element includes a pressing member disposed to wrap a wrist that is a measurement site in a circumferential direction and generating a pressing force toward the wrist, a sensing cuff that includes a second sheet disposed to face an inner circumferential surface of the pressing member and a first sheet facing the second sheet, that is formed into a bag shape for storing a pressure-transmitting fluid with circumferential edge portions of the first and second sheets brought into close contact with each other, that extends in the circumferential direction to cross an artery-passing portion of the wrist, and that allows entire areas surrounded by the circumferential edge portions of the first and second sheets to separate from each other;

a pressurization control part providing a control of compressing the wrist by the pressing member via the sensing cuff;

a fluid storage control part providing a control of supplying and storing the pressure-transmitting fluid into the sensing cuff in a worn state in which the pressing member and the sensing cuff are worn on the wrist; and a blood-pressure calculating part calculating a blood pressure based on a pressure of the pressure-transmitting fluid stored in the sensing cuff, wherein the fluid storage control part supplies the fluid in the worn state such that the first and second sheets are in contact with each other in a region corresponding to an ulna, a region corresponding to a radius, and a region corresponding to a tendon while the first and second sheets are separated from each other in regions corresponding to two arteries that are radial and ulnar arteries, and wherein the pressurization control part provides the control of compressing the wrist by the pressing member via the sensing cuff in this state.

The "device" of the present disclosure broadly includes devices having a blood-pressure measurement function and may be configured as a watch-type wearable device such as a smart watch, for example.

According to the device of the present disclosure, a blood pressure measurement value can be prevented from varying relative to an actual blood pressure, and consequently, the blood pressure can accurately be measured.

As is apparent from the above, the sphygmomanometer, the blood-pressure measurement method, and the device of the present invention can make the internal pressure of the sensing cuff equal to the pressure around the radial artery and the ulnar artery, so that the error of the blood pressure value is reduced. Therefore, a blood pressure measurement value can be prevented from varying relative to an actual blood pressure, and the blood pressure can accurately be measured.

The embodiments described above are illustrative, and various modifications can be made without departing from the scope of the present invention. Although the plurality of embodiments described above can be implemented independently of each other, the embodiments can be combined with each other. Although various features in different embodiments can be achieved independently of each other, features in different embodiments can be combined with each other.

The invention claimed is:

1. A sphygmomanometer comprising:
 a belt configured to be worn to wrap a wrist that is a measurement site in a circumferential direction;
 a bag-shaped pressing cuff disposed to face an inner circumferential surface of the belt and configured to extend along the circumferential direction of the wrist to receive a supply of a fluid and compress the wrist by generating a pressing force;
 a sensing cuff that includes a second sheet disposed to face an inner circumferential surface of the pressing cuff and a first sheet facing the second sheet, that is formed into a bag shape for storing the fluid with circumferential edge portions of the first and second sheets brought into close contact with each other, and that is configured to extend in the circumferential direction to cross an artery-passing portion of the wrist, the circumferential edge portions having two parallel long sides extending in the circumferential direction and two parallel short sides perpendicular to the two parallel long sides, the long sides and the short sides defining an entire area inside the bag shape for storing the fluid, wherein the first sheet and the second sheet are capable to separate from each other on the entire area defined by the long sides and the short sides;
a back plate interposed between the pressing cuff and the sensing cuff and configured to extend along the circumferential direction of the wrist to transmit the pressing force from the pressing cuff to the sensing cuff; and
a central processing unit that is configured to
provide a control of compressing the wrist by the pressing cuff via the sensing cuff,
provide a control of supplying and storing the fluid into the sensing cuff in a worn state in which the pressing cuff and the sensing cuff are configured to be worn on the wrist,
calculate a blood pressure based on a pressure of the fluid stored in the sensing cuff,
supply the fluid in the worn state such that the first and second sheets are in contact with each other in a region corresponding to an ulna, a region corresponding to a radius, and a region corresponding to a tendon while the first and second sheets are separated from each other in regions corresponding to two arteries that are radial and ulnar arteries, and
provide the control of compressing the wrist by the pressing cuff via the sensing cuff in this state.

2. The sphygmomanometer according to claim 1, wherein the sensing cuff is provided with sags extending along a longitudinal direction of the sensing cuff in a natural state at positions leading to edge portions on both sides of the first and second sheets in a width direction of the sensing cuff.

3. The sphygmomanometer according to claim 1, comprising a main body equipped with a pump, wherein the belt extends from the main body.

4. The sphygmomanometer according to claim 3, wherein the pressing cuff, the back plate, and the sensing cuff constitute a cuff structure having a strap shape and one end attached to the main body, and wherein
the cuff structure further includes a curler disposed along an outer circumferential surface of the pressing cuff, wherein
the curler keeps a shape of the cuff structure in a natural state configured to be curved along the circumferential direction of the wrist.

5. The sphygmomanometer according to claim 4, wherein a root portion on the main body side of the curler forming the one end of the cuff structure is sandwiched between a member disposed in the main body and a back lid of the main body, so that the one end of the cuff structure is attached to the main body.

6. The sphygmomanometer according to claim 4, wherein the other end of the cuff structure on the side opposite to the one end is a free end.

7. The sphygmomanometer according to claim 1, wherein the back plate is configured to extend in a strap shape beyond the length of the sensing cuff in the circumferential direction of the wrist, and wherein
the back plate includes a plurality of grooves having V-shaped or U-shaped cross sections, extending in the width direction of the back plate, and being parallelly separated from each other in the longitudinal direction of the back plate, which allows the back plate to curve along the circumferential direction.

8. The sphygmomanometer according to claim 3, wherein the main body is equipped with
a first flow path connecting the pump and the pressing cuff to allow the fluid to flow therebetween, and
a second flow path connecting the pump or the first flow path and the sensing cuff to allow the fluid to flow therebetween and having an on-off valve interposed therein, wherein
in the worn state, the central processing unit brings the on-off valve into an opened state and supplies and stores the fluid from the pump or the first flow path through the second flow path into the sensing cuff, and wherein
after the fluid is stored in the sensing cuff, the central processing unit brings the on-off valve into a closed state and supplies the fluid from the pump through the first flow path to the pressing cuff to compress the wrist.

9. The sphygmomanometer according to claim 4, wherein the main body is equipped with the central processing unit.

10. A blood-pressure measurement method of measuring a blood pressure of a measurement site, by a sphygmomanometer including
a belt configured to be worn to wrap a wrist that is the measurement site in a circumferential direction;
a bag-shaped pressing cuff disposed to face an inner circumferential surface of the belt and configured to extend along the circumferential direction of the wrist to receive a supply of a fluid and compress the wrist by generating a pressing force;
a sensing cuff that includes a second sheet disposed to face an inner circumferential surface of the pressing cuff and a first sheet facing the second sheet, that is formed into a bag shape for storing the fluid with circumferential edge portions of the first and second sheets brought into close contact with each other, and that is configured to extend in the circumferential direction to cross an artery-passing portion of the wrist, the circumferential edge portions having two parallel long sides extending in the circumferential direction and two parallel short sides perpendicular to the two parallel long sides, the long sides and the short sides defining an entire area inside the bag shape for storing the fluid, wherein the first sheet and the second sheet are capable to separate from each other on the entire area defined by the long sides and the short sides; and
a back plate interposed between the pressing cuff and the sensing cuff and configured to extend along the circumferential direction of the wrist to transmit the pressing force from the pressing cuff to the sensing cuff,
the method comprising:
in a worn state in which the pressing cuff and the sensing cuff are configured to be worn on the wrist,
supplying and storing the fluid into the sensing cuff such that the first and second sheets are in contact with each other in a region corresponding to an ulna, a region corresponding to a radius, and a region corresponding to a tendon while the first and second sheets are separated from each other in regions corresponding to two arteries that are radial and ulnar arteries;
providing a control in this state to compress the wrist by the pressing cuff via the sensing cuff, and
calculating a blood pressure based on a pressure of the fluid stored in the sensing cuff.

* * * * *